(12) United States Patent
Yoshida

(10) Patent No.: US 11,058,395 B2
(45) Date of Patent: Jul. 13, 2021

(54) ULTRASONIC DEVICE UNIT, ULTRASONIC PROBE, AND ULTRASONIC APPARATUS

(71) Applicant: Seiko Epson Corporation, Tokyo (JP)

(72) Inventor: Kazuki Yoshida, Fujimi (JP)

(73) Assignee: Seiko Epson Corporation

( * ) Notice: Subject to any disclaimer, the term of this patent is extended or adjusted under 35 U.S.C. 154(b) by 640 days.

(21) Appl. No.: 15/922,128

(22) Filed: Mar. 15, 2018

(65) Prior Publication Data

US 2018/0271489 A1 Sep. 27, 2018

(30) Foreign Application Priority Data

Mar. 22, 2017 (JP) .............................. JP2017-055391

(51) Int. Cl.
*A61B 8/00* (2006.01)
*H05K 1/18* (2006.01)
*B06B 1/06* (2006.01)
*A61B 8/06* (2006.01)

(52) U.S. Cl.
CPC .......... *A61B 8/4455* (2013.01); *A61B 8/4494* (2013.01); *A61B 8/54* (2013.01); *B06B 1/0607* (2013.01); *B06B 1/0622* (2013.01); *H05K 1/184* (2013.01); *H05K 1/189* (2013.01); *A61B 8/06* (2013.01); *A61B 8/461* (2013.01)

(58) Field of Classification Search
CPC ........ A61B 8/54; A61B 8/4494; H05K 1/189; H05K 1/184; B06B 1/0607
See application file for complete search history.

(56) References Cited

U.S. PATENT DOCUMENTS 6,183,419 B1 * 2/2001 Wildes ................ G01S 7/52046
600/447
2014/0290371 A1 * 10/2014 Nakamura ............ B06B 1/0629
73/644

FOREIGN PATENT DOCUMENTS

JP 2016-092592 A 5/2016

* cited by examiner

*Primary Examiner* — Jason M Ip
(74) *Attorney, Agent, or Firm* — Harness, Dickey & Pierce, P.L.C.

(57) ABSTRACT

An ultrasonic device unit includes an ultrasonic device including 1-st through n-th vibrator elements and 1-st through n-th device-side terminals connected corresponding respectively to the vibrator elements, and a flexible printed wiring board to be connected to the ultrasonic device, in which the flexible printed wiring board includes a first connector section provided with 1-st through k-th external connection terminals, a second connector section provided with (k+1)-th through n-th external connection terminals, a device connection section which is disposed between the first connector section and the second connector section, and to which the 1-st through n-th device-side terminals are connected, and interconnections adapted to connect the i-th device-side terminal and the i-th external connection terminal to each other.

12 Claims, 14 Drawing Sheets

ULTRASONIC DEVICE UNIT, ULTRASONIC PROBE, AND ULTRASONIC APPARATUS

BACKGROUND

1. Technical Field

The present invention relates to an ultrasonic device unit, an ultrasonic probe, and an ultrasonic apparatus.

2. Related Art

In the past, there has been known an ultrasonic device unit having an ultrasonic element array in which ultrasonic elements for performing transmission and reception of ultrasonic waves are arranged (see, e.g., JP-A-2016-92592 (Document 1)).

The ultrasonic device unit of Document 1 is provided with the ultrasonic device having terminals corresponding respectively to the ultrasonic elements, and the ultrasonic device is connected to a device terminal via a flexible printed wiring board (a flexible board).

The flexible board is provided with a first flat-plate part disposed on one end side with respect to the center line, and the ultrasonic device is fixed to the first flat-plate part. Further, the flexible board is provided with a second flat-plate part disposed on the other end side with respect to the center line, and connecters to which the terminals of the ultrasonic device are connected are disposed in the second flat-plate part. Further, the terminals on the second flat-plate part side of the ultrasonic device are connected to the connector with interconnections formed on the reverse surfaces of the first flat-plate part through the second flat-plate part. In contrast, the terminals on the opposite side to the second flat-plate part of the ultrasonic device are connected to the connector with first interconnections extending from the reverse surface to the obverse surface of the first flat-plate part, second interconnections connected respectively to the first interconnections and extending from the obverse surface of the first flat-plate part to the obverse surface of the second flat-plate part, and third interconnections connected respectively to the second interconnections and extending from the obverse surface of the second flat-plate part to the reverse surface of the second flat-plate part and then extending to the connector.

Incidentally, in the ultrasonic device unit described in Document 1, the length of the interconnections from the terminals disposed on the opposite side to the second flat-plate part of the ultrasonic device to the connector is longer than the length of the interconnections from the terminals disposed on the second flat-plate part side of the ultrasonic device to the connector. In general, in the case in which the length of the interconnections from the ultrasonic device to the connector is long, the voltage value of a drive signal is lowered due to the voltage drop, and appropriate transmission and reception of the ultrasonic wave become unachievable in the ultrasonic device.

For example, in the ultrasonic device unit described in Document 1, in the case of inputting the drive signals with the same voltage value to the terminals, the acoustic pressure of the ultrasonic wave output from the ultrasonic element connected to the terminal on the opposite side to the second flat-plate part of the ultrasonic device becomes lower compared to that of the ultrasonic element connected to the terminal on the second flat-plate part side. Therefore, the acoustic pressure of the ultrasonic waves output from the ultrasonic device becomes non-uniform.

SUMMARY

An advantage of the invention is to provide an ultrasonic device unit, an ultrasonic probe, and an ultrasonic apparatus capable of outputting an appropriate ultrasonic wave from an ultrasonic device.

An ultrasonic device unit of an application example according to the invention includes an ultrasonic device including 1-st through n-th (n is an integer no smaller than 2) vibrator elements and 1-st through n-th device-side terminals connected corresponding respectively to the vibrator elements, and a flexible printed wiring board to be connected to the ultrasonic device, in which the flexible printed wiring board includes a first connector section provided with 1-st through k-th (k is an integer satisfying $1 \leq k < n$) external connection terminals, a second connector section provided with (k+1)-th through n-th external connection terminals, a device connection section which is disposed between the first connector section and the second connector section, and to which the 1-st through n-th device-side terminals are connected, and interconnections provided corresponding respectively to the 1-st through n-th device-side terminals and the 1-st through n-th external connection terminals, and adapted to connect the i-th device-side terminal and the i-th external connection terminal to each other.

In this application example, the flexible printed wiring board includes the device connection section, the first connector section, and the second connector section. Further, the k device-side terminals, namely the 1-st through k-th device-side terminals, of the ultrasonic device are connected to the external connection terminals of the first connector section with the interconnections extending from the device connection section to the external connection terminals, and the n-k device-side terminals, namely the (k+1)-th through n-th device-side terminals, are connected to the external connection terminals of the second connector section with the interconnections extending from the device connection section to the external connection terminals.

In such a configuration, the influence of the voltage drop due to the interconnections can be suppressed compared to the case in which, for example, the external connection terminals are provided only to the first connector section. Specifically, in the case in which the external connection terminals are provided only to the first connector section, it is necessary to form the interconnections so as not to cross each other. In the device connection section to which the ultrasonic device is connected, the device-side terminals located on the first connector section side are connected to the external connection terminals located on the device connection section side of the first connector section. However, as the position of the device-side terminal gets away from the first connector section, the position of the external connection terminal to be connected also gets away from the device connection section, and the interconnection elongates accordingly. Therefore, in the ultrasonic device, the transmission/reception efficiency of the ultrasonic wave due to the vibrator element is high on the side close to the first connector section, and the transmission/reception efficiency lowers as the distance from the first connector section increases.

In contrast, in this application example, there are provided the first connector section and the second connector section. In this case, the device-side terminals located distantly from the first connector section can be connected to the external connection terminals of the second connector section. Therefore, there is no interconnection with the wiring length extremely elongated, and it is also possible to suppress the influence of the voltage drop on the transmission/reception efficiency. Thus, in the ultrasonic device, an appropriate transmission and reception of the ultrasonic wave can be achieved.

In the ultrasonic device unit according to the application example, it is preferable that the vibrator elements each include a plurality of ultrasonic elements arranged in a first direction, the vibrator elements are arranged in a second direction crossing the first direction, the device-side terminals include first device-side terminals disposed on one end side in the first direction of the vibrator elements, and second device-side terminals disposed on the other end side in the first direction, and the i-th first device-side terminal and the i-th second device-side terminal are connected to the i-th external connection terminal.

In the application example with this configuration, the vibrator elements each include a plurality of ultrasonic elements arranged in a first direction. In such a configuration, when the drive signal is input from one side in the first direction, the drive characteristics (the transmission/reception efficiency) of the ultrasonic element disposed on the other side is lowered due to the influence of the voltage drop. In contrast, in the present application example, the first device-side terminals are disposed on one end side in the first direction, the second device-side terminals are disposed on the other end side, and both of the first device-side terminals and the second device-side terminals are connected to the same external connection terminals, respectively. In this case, it results that the same drive signal is input from the both end sides of the ultrasonic element disposed in the first direction, and it is possible to suppress the influence of the voltage drop.

In the ultrasonic device unit according to the application example, it is preferable that in the flexible printed wiring board, the first connector section, the device connection section, and the second connector section are arranged along the second direction.

In the application example with this configuration, it is possible to form the interconnections extending from the device connection section toward the first connector section, and the interconnections extending from the device connection section toward the second connector section so as to have symmetrical shapes. In this case, since the lengths of the interconnections also become symmetrical with each other, even in the case in which the voltage drop occurs, the transmission/reception efficiency of the ultrasonic wave output from the first connector section side in the ultrasonic device and the transmission/reception efficiency of the ultrasonic wave output from the second connector section side become roughly equal to each other. Therefore, it is prevented that the transmission/reception efficiency of the ultrasonic wave significantly lowers in a part of the ultrasonic device, and the appropriate transmission/reception process of the ultrasonic wave can be performed.

Further, as described above, in the configuration provided with the interconnections connected to the first device-side terminals and the interconnections connected to the second device-side terminals, if, for example, the first connector section is disposed in the first direction from the device connection section, and the second connector section is disposed in the second direction from the device connection section, the interconnections connected to the first device-side terminals and the interconnections connected to the second device-side terminals become different in length dimension from each other.

In contrast, in the application example with the configuration described above, it is possible to dispose the interconnections to be connected to the first device-side terminals and the interconnections to be connected to the second device-side terminals so as to have symmetrical shapes. Therefore, the influence of the voltage drop becomes roughly the same between the interconnections to be connected to the first device-side terminals and the interconnections to be connected to the second device-side terminals, and thus, the drive signal input to the first device-side terminal of the vibrator element and the drive signal input to the second device-side terminal can be made roughly equal to each other. Thus, it is possible to equalize the transmission/reception efficiency of the ultrasonic wave due to the vibrator elements, and it is possible to perform an appropriate transmission/reception process of the ultrasonic wave.

In the ultrasonic device unit according to the application example, it is preferable that $|(n-k)-k|/n \leq 0.2$ is fulfilled.

In the application example with this configuration, the difference between the number of the device-side terminals to be connected to the external connection terminal of the first connector section and the number of the device-side terminals to be connected to the external connection terminals of the second connector section becomes equal to or lower than 20% of the total number of the device-side terminals. If the difference between the number of the device-side terminals to be connected to the first connector section and the number of the device-side terminals to be connected to the second connector section exceeds 20%, the number of the vibrator elements significantly affected by the voltage drop due to the increase in length dimension of the interconnections increases. For example, in the case in which 100 vibrator elements are connected to the external connection terminals of the first connector section, and 200 vibrator elements are connected to the external connection terminals of the second connector section, the number of the interconnections extending from the device connection section toward the second connector section increases, and the lengths of some of the interconnections extending from the device connection section toward the second connector section increase. Therefore, the influence of the voltage drop in some vibrator elements long in interconnection length increases, and thus, the transmission/reception efficiency in the vibrator element decreases.

In contrast, by adopting the configuration described above, it is possible to reduce the number of the vibrator elements significantly affected by the voltage drop.

In the ultrasonic device unit according to the application example, it is preferable that $k=n/2$ is fulfilled.

In the application example with this configuration, the number of the device-side terminals to be connected to the external connection terminal of the first connector section and the number of the device-side terminals to be connected to the external connection terminals of the second connector section are equal to each other. Therefore, between the vibrator elements to be connected to the first connector section and the vibrator elements to be connected to the second connector section, the influence of the voltage drop can be made roughly the same, and thus, the transmission/reception efficiency of the ultrasonic wave in the ultrasonic device can be equalized.

An ultrasonic probe according to an application example of the invention includes the ultrasonic device unit according to any one of the application examples described above, and a housing adapted to store the ultrasonic device unit.

In the ultrasonic probe according to this application example, such an ultrasonic device unit as described above is housed in the housing, and by making the ultrasonic probe have contact with the test object, the ultrasonic measurement on the test object can be performed. Further, as described above, since the ultrasonic device unit is suppressed in the influence of the voltage drop, and can therefore perform the appropriate transmission/reception process of the ultrasonic wave, also in the ultrasonic probe equipped with the ultrasonic device unit, the highly accurate ultrasonic measurement can be performed.

An ultrasonic apparatus according to an application example of the invention includes the ultrasonic device unit according to any one of the application examples described above, and a control section adapted to control the ultrasonic device unit.

In this application example, by controlling such an ultrasonic device unit as described above, it is possible to perform a variety of types of ultrasonic processing (e.g., ultrasonic measurement on the test object, and ultrasonic therapy on the test object) in accordance with the measurement result of the ultrasonic measurement. Further, as described above, since the ultrasonic device unit is suppressed in the influence of the voltage drop, and can therefore perform the appropriate transmission/reception process of the ultrasonic wave, also in the ultrasonic device equipped with such an ultrasonic device unit, the ultrasonic measurement described above can be performed with high accuracy.

BRIEF DESCRIPTION OF THE DRAWINGS

The invention will be described with reference to the accompanying drawings, wherein like numbers reference like elements.

DESCRIPTION OF AN EXEMPLARY EMBODIMENT

An embodiment according to the invention will hereinafter be described.

Figure 1:
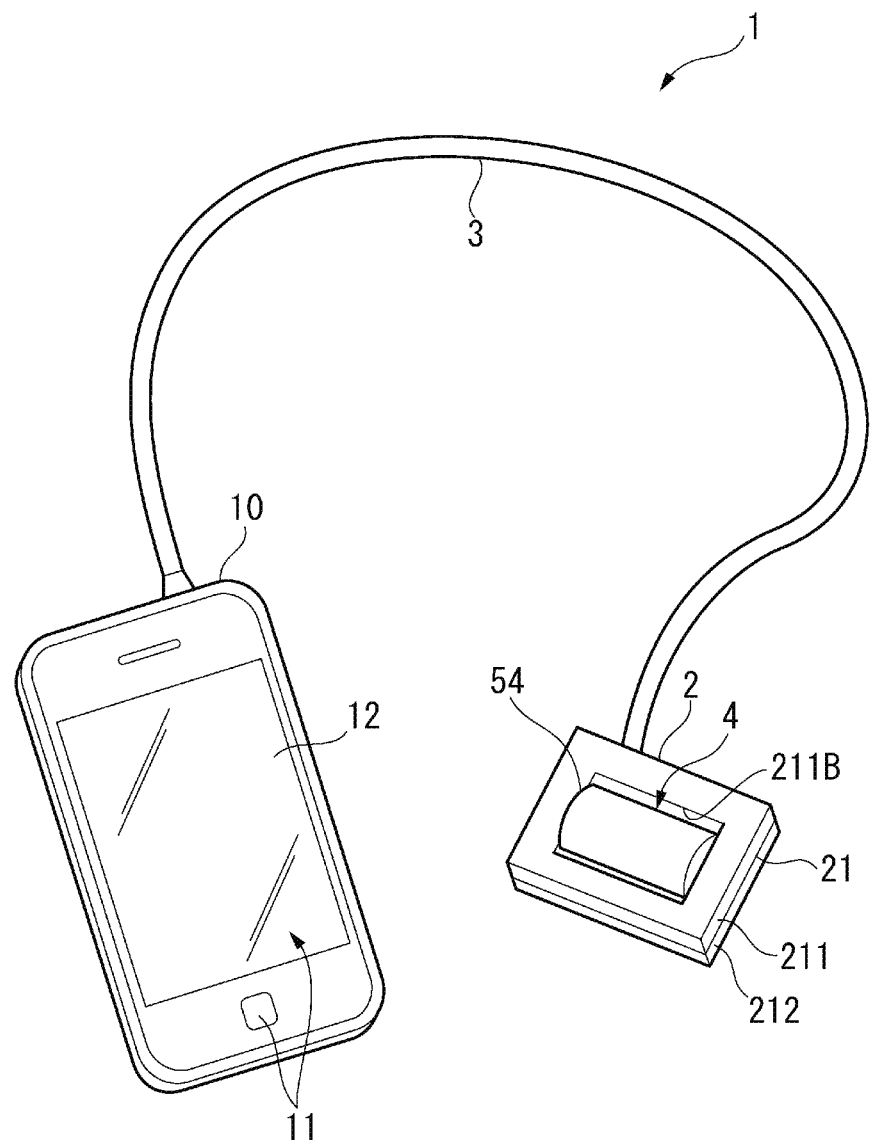
FIG. 1 is a perspective view showing a schematic configuration of an ultrasonic measurement apparatus according to an embodiment of the invention.

FIG. 1 is a perspective view showing a schematic configuration of the ultrasonic measurement apparatus 1.

As shown in FIG. 1, the ultrasonic measurement apparatus 1 corresponds to an ultrasonic apparatus, and is provided with an ultrasonic probe 2, and a control device 10 electrically connected to the ultrasonic probe 2 via a cable 3.

The ultrasonic measurement apparatus 1 transmits an ultrasonic wave from the ultrasonic probe 2 to the inside of a living body (e.g., a human body) in the state in which the ultrasonic probe 2 has contact with a surface of the living body. Further, the ultrasonic measurement apparatus 1 receives the ultrasonic wave reflected by an organ in the living body using the ultrasonic probe 2, and then, for example, obtains an internal tomographic image of the inside of the living body to measure the state (e.g., blood flow) of the organ in the living body based on the received signal.

1. Configuration of Control Device

As shown in FIG. 1, for example, the control device 10 corresponds to a control section, and is provided with an operating section 11 including buttons or a touch panel, and a display section 12. Further, although not shown in the drawings, the control device 10 is provided with a storage section formed of a memory and so on, and an arithmetic section constituted by a central processing unit (CPU) and so on. The control device 10 makes the arithmetic section execute a variety of programs stored in the storage section to thereby control the ultrasonic measurement apparatus 1. For example, the control device 10 outputs a command for controlling the drive of the ultrasonic probe 2, forms an image of the internal structure of the living body and then makes the display section 12 display the image, and measures the living body information such as the blood flow to make the display section 12 display the living body information based on the received signal input from the ultrasonic probe 2. As such a control device 10, there can be used a terminal device such as a tablet terminal, a smartphone, or a personal computer, and a dedicated terminal device for operating the ultrasonic probe 2 can also be used.

2. Configuration of Ultrasonic Probe

Figure 2:
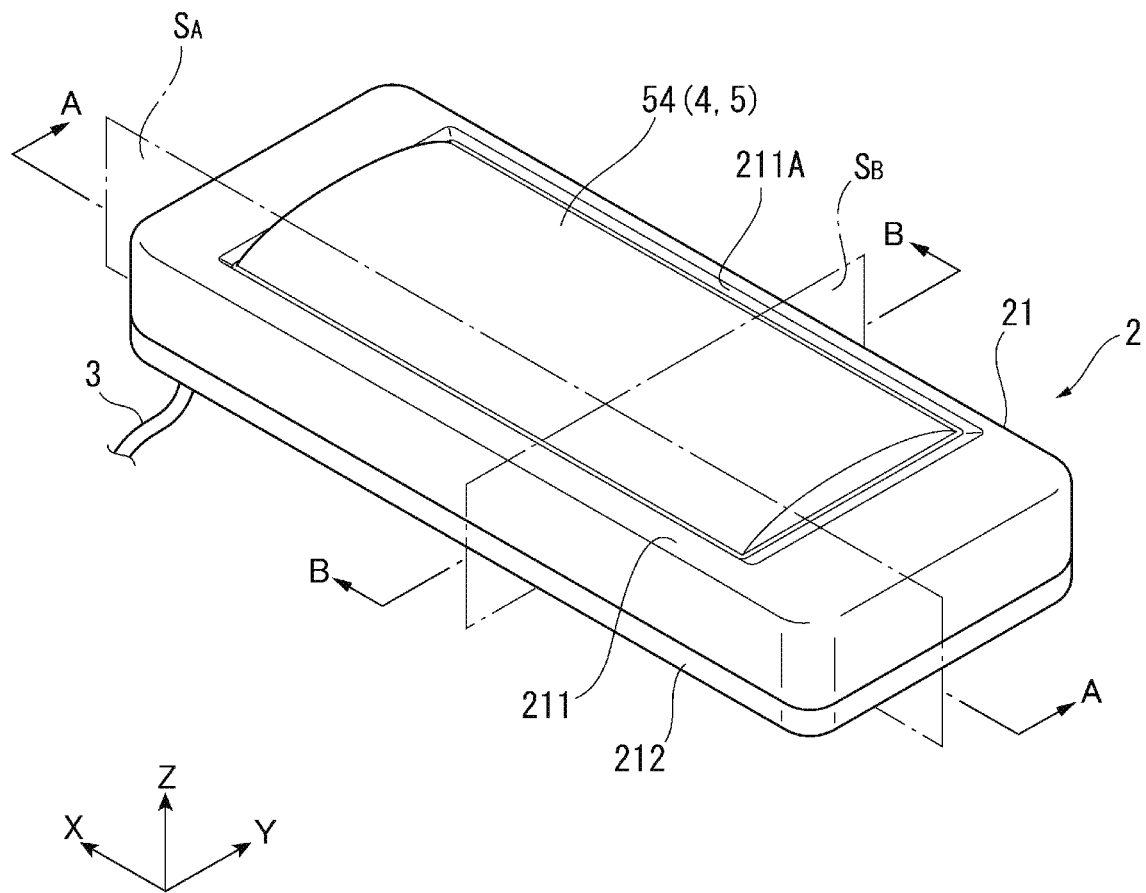
FIG. 2 is a perspective view showing an appearance of an ultrasonic probe according to the embodiment.
Figure 3:
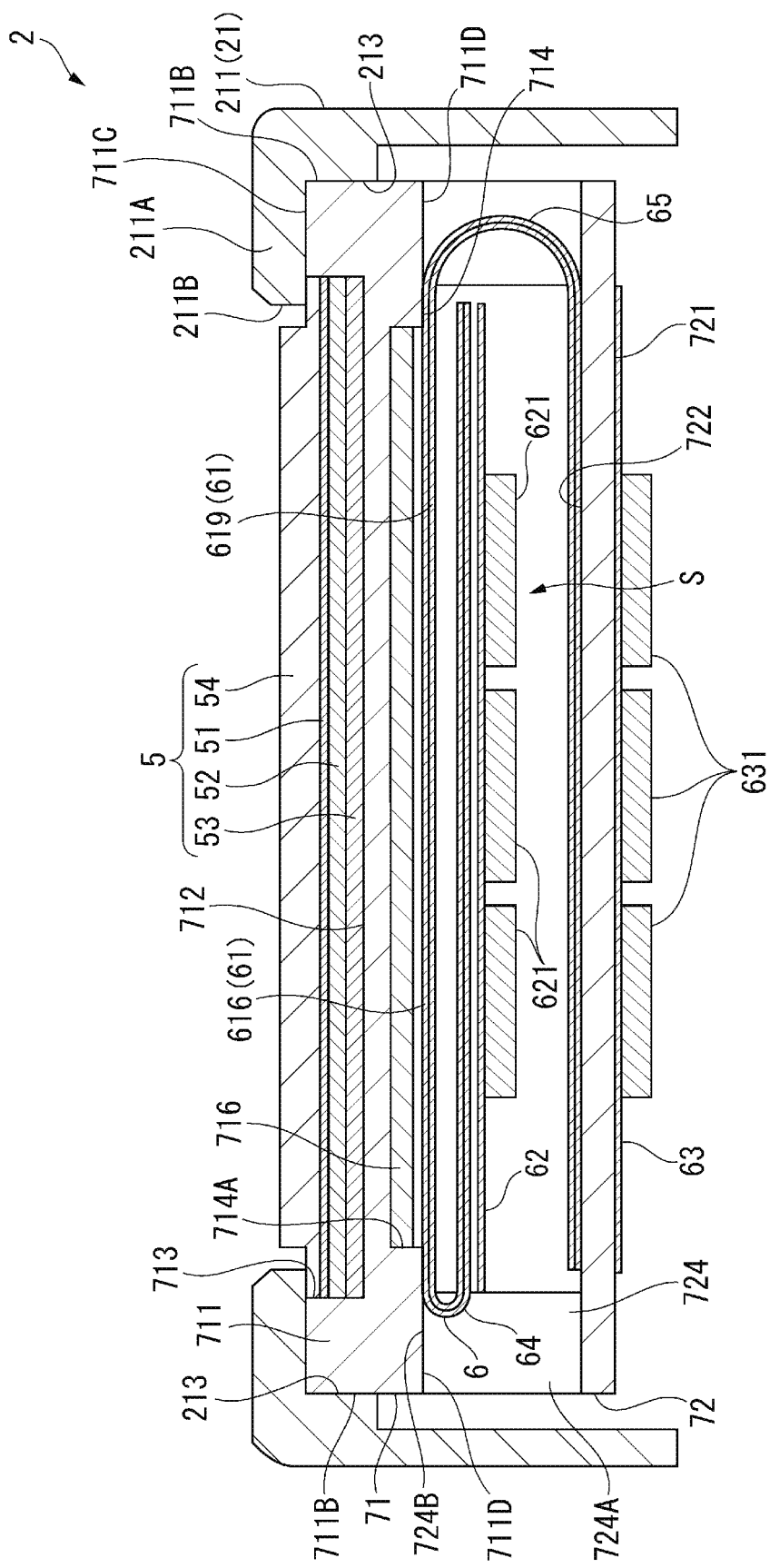
FIG. 3 is a cross-sectional view of the ultrasonic probe cut along the line A-A shown in FIG. 2.
Figure 4:
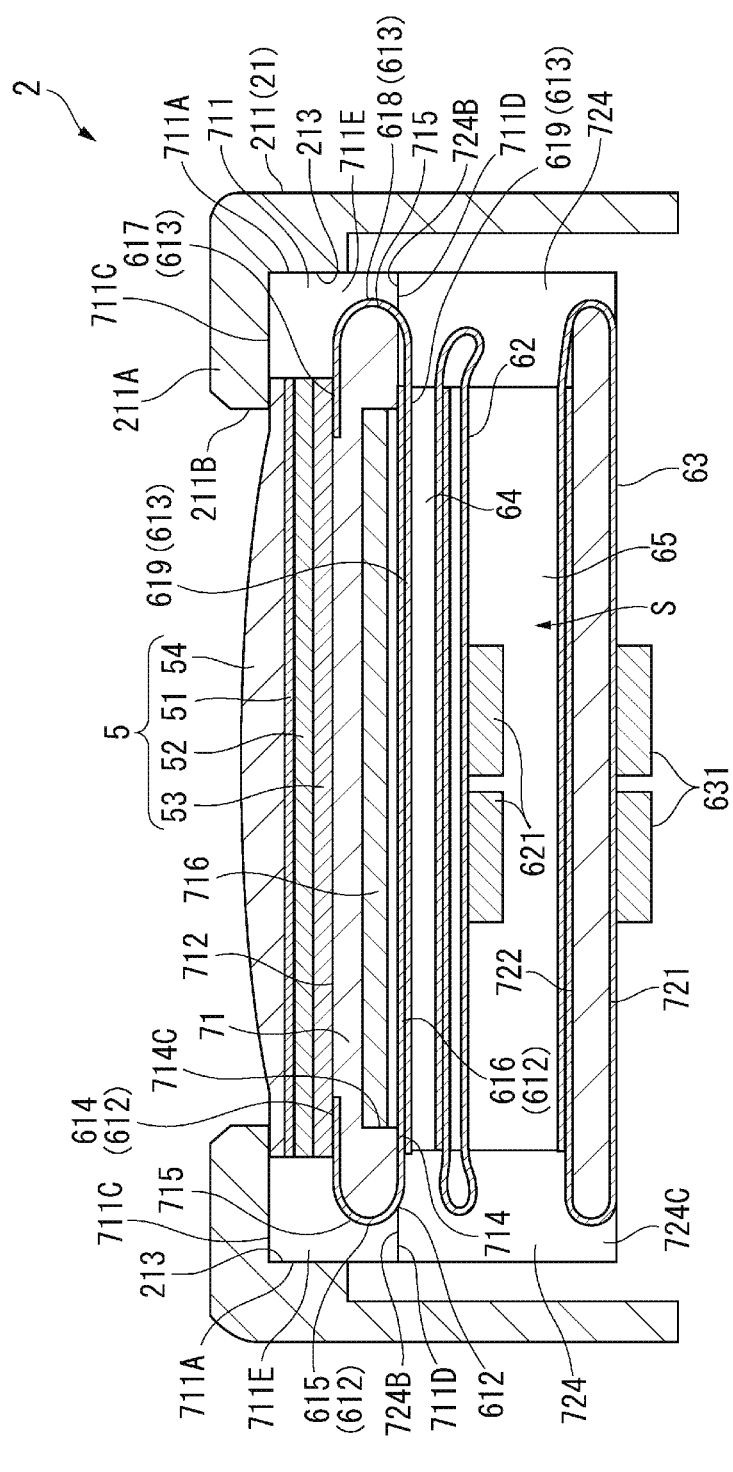
FIG. 4 is a cross-sectional view of the ultrasonic probe cut along the line B-B shown in FIG. 2.

FIG. 2 is a perspective view showing an appearance of the ultrasonic probe 2. FIG. 3 is a cross-sectional view of the ultrasonic probe 2 cut along the line A-A (a plane $S_A$) shown in FIG. 2, and FIG. 4 is a cross-sectional view of the ultrasonic probe 2 cut along the line B-B (a plane $S_B$) shown in FIG. 2.

The ultrasonic probe 2 corresponds to an ultrasonic probe, and is provided with a housing 21, and an ultrasonic device unit 4 stored inside the housing 21 as shown in FIG. 1 through FIG. 4. Further, the ultrasonic device unit 4 is configured including an ultrasonic device 5, a flexible printed wiring board (a flexible board 6), a first reinforcing plate 71, and a second reinforcing plate 72.

Hereinafter, each of the constituents will be described in detail.

2-1. Configuration of Ultrasonic Device 5

As shown in FIG. 3 and FIG. 4, the ultrasonic device constituting the ultrasonic device unit 4 includes an ultrasonic substrate 51, a sealing plate 52, a wiring board 53, and an acoustic lens 54, and is formed by stacking the wiring board 53, the sealing plate 52, the ultrasonic substrate 51, and the acoustic lens 54 in this order. In the present embodiment, the ultrasonic device 5 is formed to have, for example, a rectangular shape in a planar view viewed from the stacking direction (a Z direction) of the wiring board 53, the sealing plate 52, the ultrasonic substrate 51, and the acoustic lens 54.

2-1-1. Configuration of Ultrasonic Substrate 51

Figure 5:
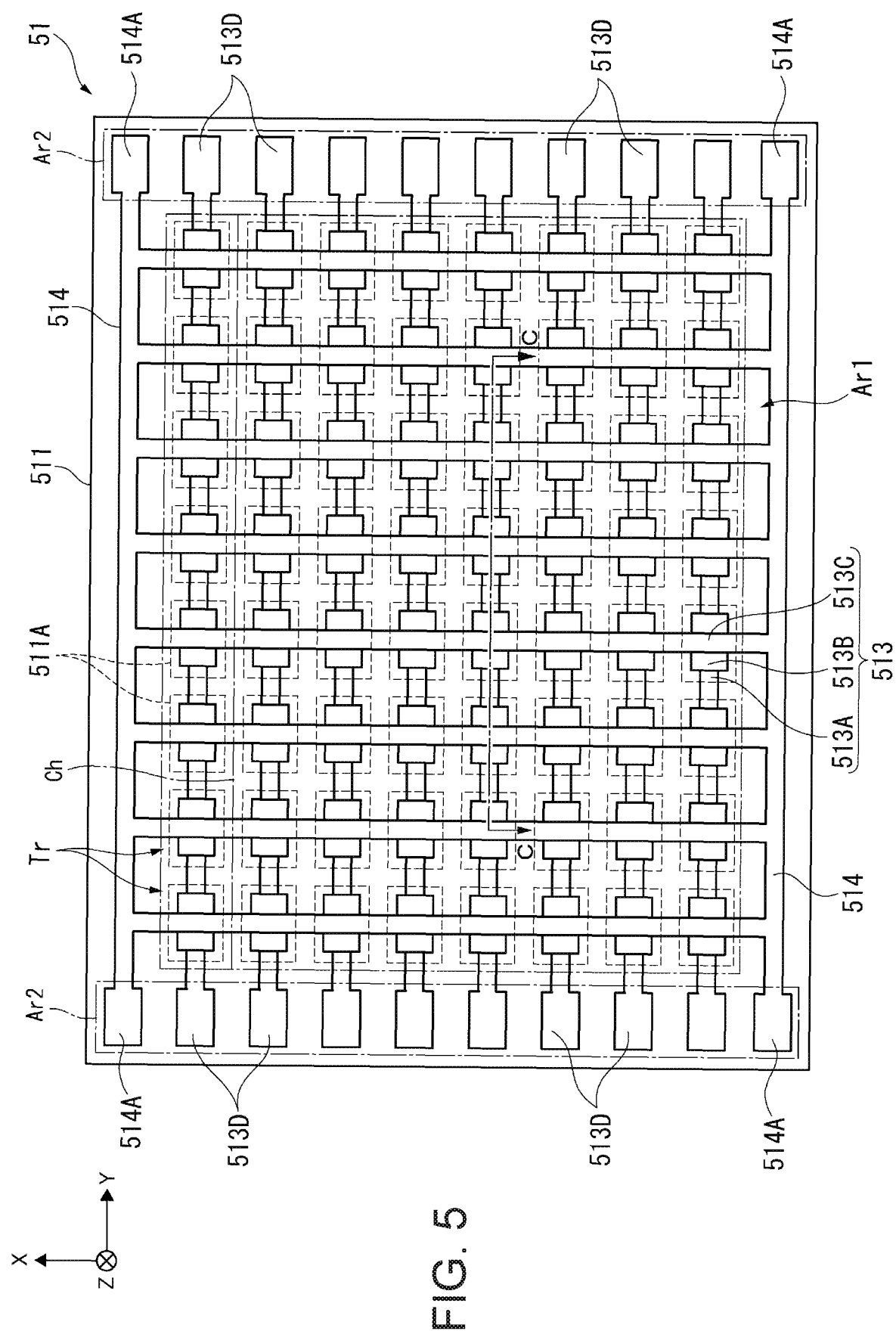
FIG. 5 is a plan view showing a schematic configuration of an ultrasonic substrate of the embodiment.

FIG. 5 is a plan view showing a schematic configuration of the ultrasonic substrate 51 of the present embodiment.

As shown in FIG. 5, the ultrasonic substrate 51 is provided with a plurality of ultrasonic transducers Tr arranged in a two-dimensional array along the X direction (a second direction, a scanning direction) and the Y direction (a first direction, a slicing direction). In the present embodiment, 1-CH (channel) transmission/reception column Ch (vibrator element) is constituted by a plurality of ultrasonic transducers Tr (ultrasonic elements) arranged in the Y direction. Further, a plurality of the 1-CH transmission/reception columns Ch arranged side by side along the X direction constitutes the ultrasonic substrate 51 having a two-dimensional array structure. Here, in the ultrasonic substrate 51, an area where the ultrasonic transducers Tr are arranged is defined as an array area Ar1.

It should be noted that in FIG. 5, the number of the ultrasonic transducers Tr arranged is reduced for the sake of convenience of explanation, but in reality, there are arranged a larger number of ultrasonic transducers Tr.

Figure 6:
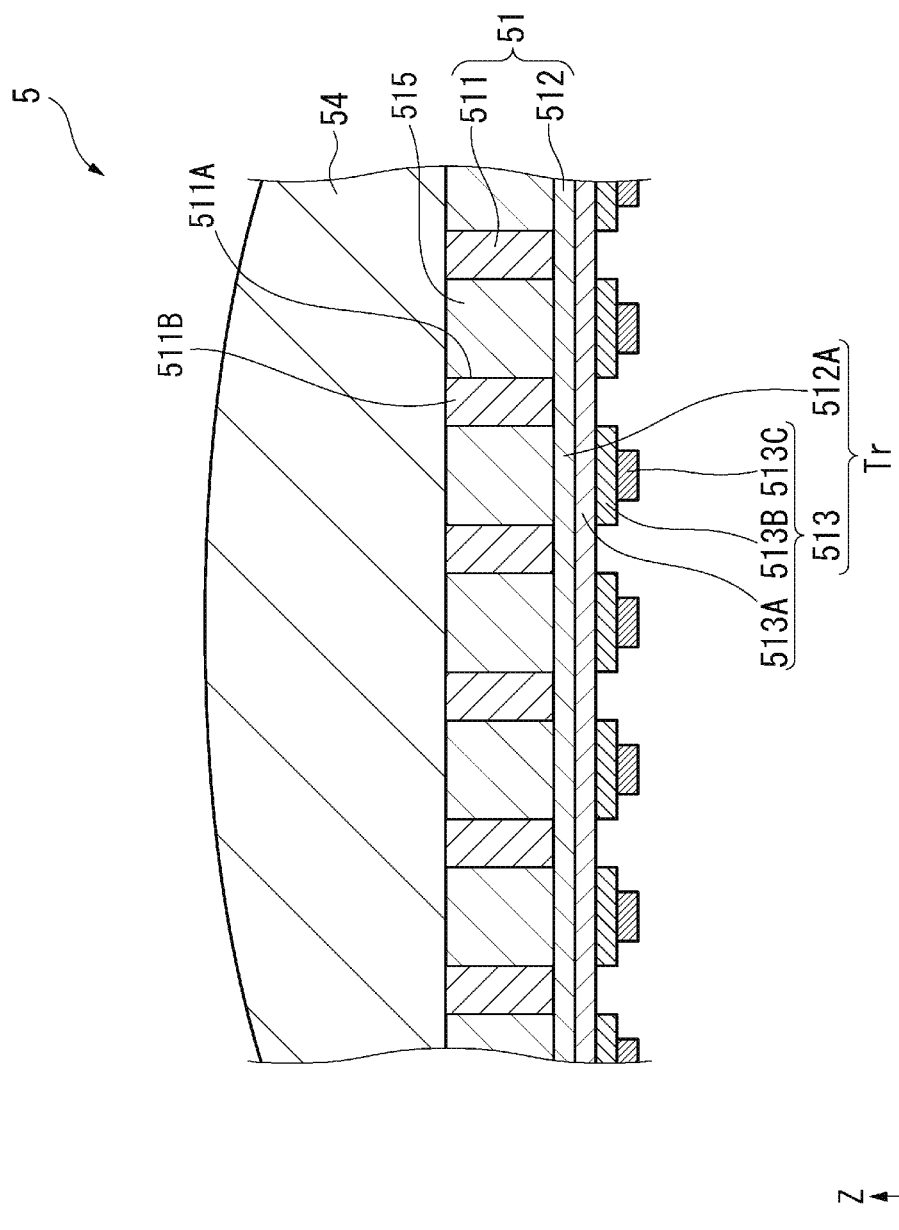
FIG. 6 is a cross-sectional view of the ultrasonic substrate cut along the line C-C shown in FIG. 5.

FIG. 6 is a schematic cross-sectional view of the ultrasonic substrate 51 cut along the line C-C shown in FIG. 5.

As shown in FIG. 6, the ultrasonic substrate 51 is configured including an element substrate 511, a support film 512 disposed on the element substrate 511, and piezoelectric elements 513 disposed on the support film 512.

The element substrate 511 is formed of a semiconductor substrate made of, for example, Si. The element substrate 511 is provided with substrate opening parts 511A corresponding to the respective ultrasonic transducers Tr. In the present embodiment, each of the substrate opening parts 511A is a through hole penetrating the element substrate 511 in the thickness direction thereof, and the support film 512 is disposed on one end side (the sealing plate 52 side) of the through hole.

Further, the side of the substrate opening part 511A where the support film 512 is not provided is filled with an acoustic layer 515 having acoustic impedance approximate to that of the living body.

Further, on a surface of the element substrate 511 located on the opposite side to the support film 512, there is disposed the acoustic lens 54 having contact with the element substrate 511 and the acoustic layer 515. The acoustic lens 54 is a part which is exposed from the sensor window 211B (see FIG. 1 and so on) provided to the housing 21 when the ultrasonic device unit 4 is stored in the housing 21, and forms a part to have contact with the test object when performing the ultrasonic measurement. Similarly to the acoustic layer 515, the acoustic lens 54 is formed of, for example, silicone having acoustic impedance approximate to that of the living body, and is formed to have a cylindrical shape with an axis parallel to the X direction.

The support film 512 is formed of, for example, a stacked body of $SiO_2$ and $ZrO_2$, and is disposed so as to cover the entire area on the sealing plate 52 side of the element substrate 511. Specifically, the support film 512 is supported by partition walls 511B constituting the substrate opening parts 511A, and closes the sealing plate 52 side of the substrate opening parts 511A. The thickness dimension of the support film 512 is made sufficiently small with respect to that of the element substrate 511.

It should be noted that in the present embodiment, the support film 512 is formed by performing a thermal oxidation treatment on one surface of the element substrate 511 formed of Si to form $SiO_2$, and then stacking $ZrO_2$ thereon. On this occasion, by performing etching on the element substrate 511 using the support film 512 including $SiO_2$ as an etching stopper, it becomes possible to easily form the substrate opening parts 511A and the partition walls 511B.

The piezoelectric elements 513 are disposed on respective parts of the support film 512 closing the respective substrate opening parts 511A. The piezoelectric elements 513 are each formed of, for example, a stacked body obtained by stacking a lower-part electrode 513A, a piezoelectric film 513B, and an upper-part electrode 513C from the support film 512 side.

Here, the part of the support film 512 closing the substrate opening part 511A constitutes a vibrating part 512A, and the vibrating part 512A and the piezoelectric element 513 constitute one ultrasonic transducer Tr.

In such an ultrasonic transducer Tr, by applying a rectangular-wave voltage (a drive voltage) having a predetermined frequency between the lower-part electrode 513A and the upper-part electrode 513C, the piezoelectric film 513B is deflected to vibrate the vibrating part 512A to transmit the ultrasonic wave. Further, when the vibrating part 512A is vibrated by the ultrasonic wave (a reflected wave) reflected by the living body, an electrical potential difference occurs between an upper part and a lower part of the piezoelectric film 513B. Thus, by detecting the electrical potential difference occurring between the lower-part electrode 513A and the upper-part electrode 513C, it becomes possible to detect the ultrasonic wave received.

As shown in FIG. 5, in the present embodiment, the lower-part electrode 513A is formed along the Y direction to have a linear shape, and connects the plurality of ultrasonic transducers Tr constituting the 1-CH transmission/reception column Ch to each other. Drive terminals 513D therefor are electrically connected to the wiring board 53 via, for example, through electrodes provided to the sealing plate 52.

Further, the upper-part electrode 513C is formed along the X direction to form a linear shape, and connects the ultrasonic transducers Tr arranged in the X direction. Further, the end parts on the ±X sides of the upper-part electrode 513C are respectively connected to common electrode lines 514. The common electrode lines 514 each connect the upper-part electrodes 513C arranged along the Y direction to each other, and are each provided with common terminals 514A at the end parts thereof, wherein the common terminals 514A are electrically connected to the wiring board 53. The common terminals 514A are electrically connected to the wiring board 53 with, for example, through electrodes provided to the sealing plate 52.

2-1-2. Configuration of Sealing Plate 52

The sealing plate 52 is formed so that the planar shape of the sealing plate 52 viewed from the thickness direction has the same shape as that of, for example, the ultrasonic substrate 51. Further, the sealing plate 52 is bonded with a fixation member such as resin on the support film 512 side of the ultrasonic substrate 51, and at the positions overlapping the partition walls 511B viewed from the substrate thickness direction, to reinforce the ultrasonic substrate 51.

The sealing plate 52 is provided with openings not shown at positions opposed to the drive terminals 513D and the common terminals 514A of the element substrate 511, and through electrodes 521 (see FIG. 7), for example, for connecting the drive terminals 513D and the common terminals 514A to the wiring board 53 are inserted through the openings.

2-1-3. Configuration of Wiring Board 53

Figure 7:
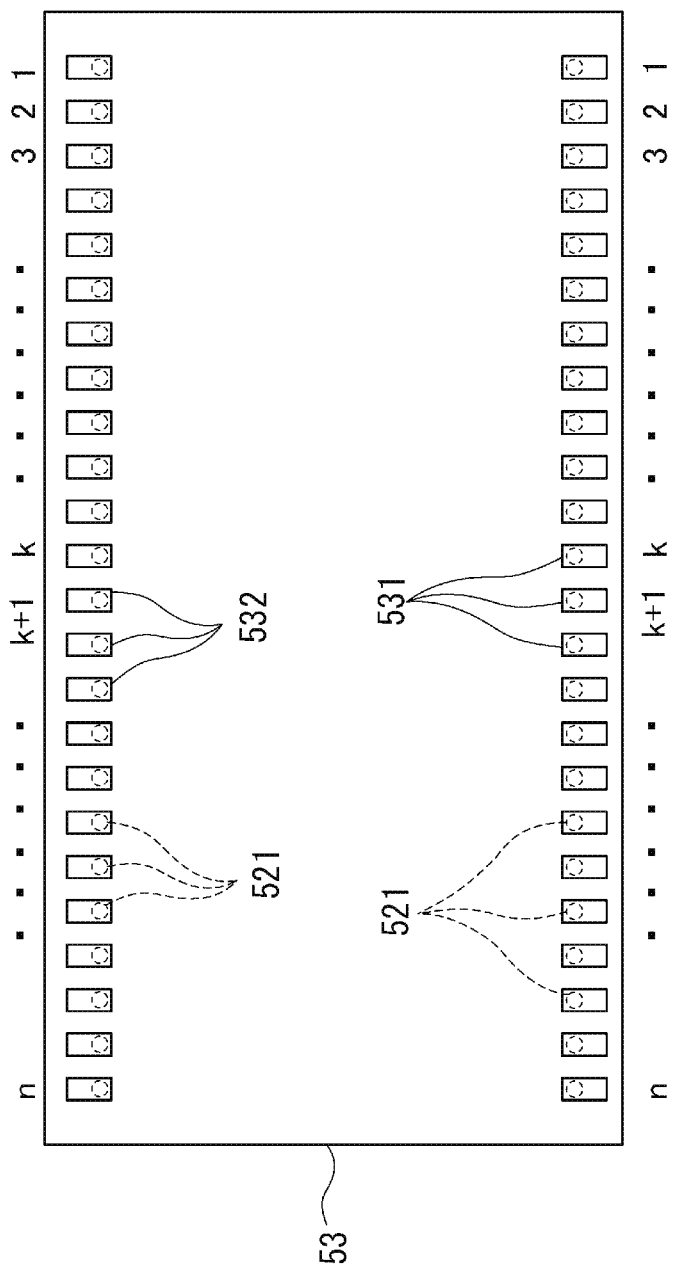
FIG. 7 is a plan view showing a schematic configuration of a wiring board of the embodiment.

FIG. 7 is a plan view showing a schematic configuration of the wiring board 53.

As shown in FIG. 7, the wiring board 53 is provided with device-side terminals (first device-side terminals 531 and second device-side terminals 532) at positions opposed to the drive terminals 513D and the common terminals 514A. These device-side terminals are connected to the drive terminals 513D and the common terminals 514A via the through electrodes 521 provided to the sealing plate 52, respectively.

In the present embodiment, the drive terminals 513D and the common terminals 514A are disposed in the both end parts (Ar2) of the flexible board 6 in the Y direction as shown in FIG. 5. Therefore, also in the wiring board 53, the device-side terminals corresponding to the drive terminals 513D and the common terminals 514A are disposed in the both end parts in the Y direction. Here, in the following description, the device-side terminals disposed on the −Y side are referred to as first device-side terminals 531, and the device-side terminals disposed on the +Y side as the other end side in the Y direction are referred to as second device-side terminals 532.

Further, in the present embodiment, the number of each of the first device-side terminals 531 and the second device-side terminals 532 provided to the wiring substrate 53 is n (n is an integer equal to or greater than 2). Here, the first device-side terminal disposed at the −X side end part is defined as a 1-st first device-side terminal 531, the second device-side terminal disposed at the −X side end part is defined as a 1-st second device-side terminal 532, the first device-side terminal disposed at the +X side end part is defined as an n-th first device-side terminal 531, and the second device-side terminal disposed at the +X side end part is defined as an n-th second device-side terminal 532. The first device-side terminal 531 and the second device-side terminal 532 disposed at "i"-th position from the −X side end part are defined as an i-th first device-side terminal 531 and an i-th second device-side terminal 532, respectively.

To each of the first device-side terminals 531 and the second device-side terminals 532, there is connected the flexible board 6.

2-2. Configuration of Flexible Printed Wiring Board (Flexible Board 6)

Figure 8:
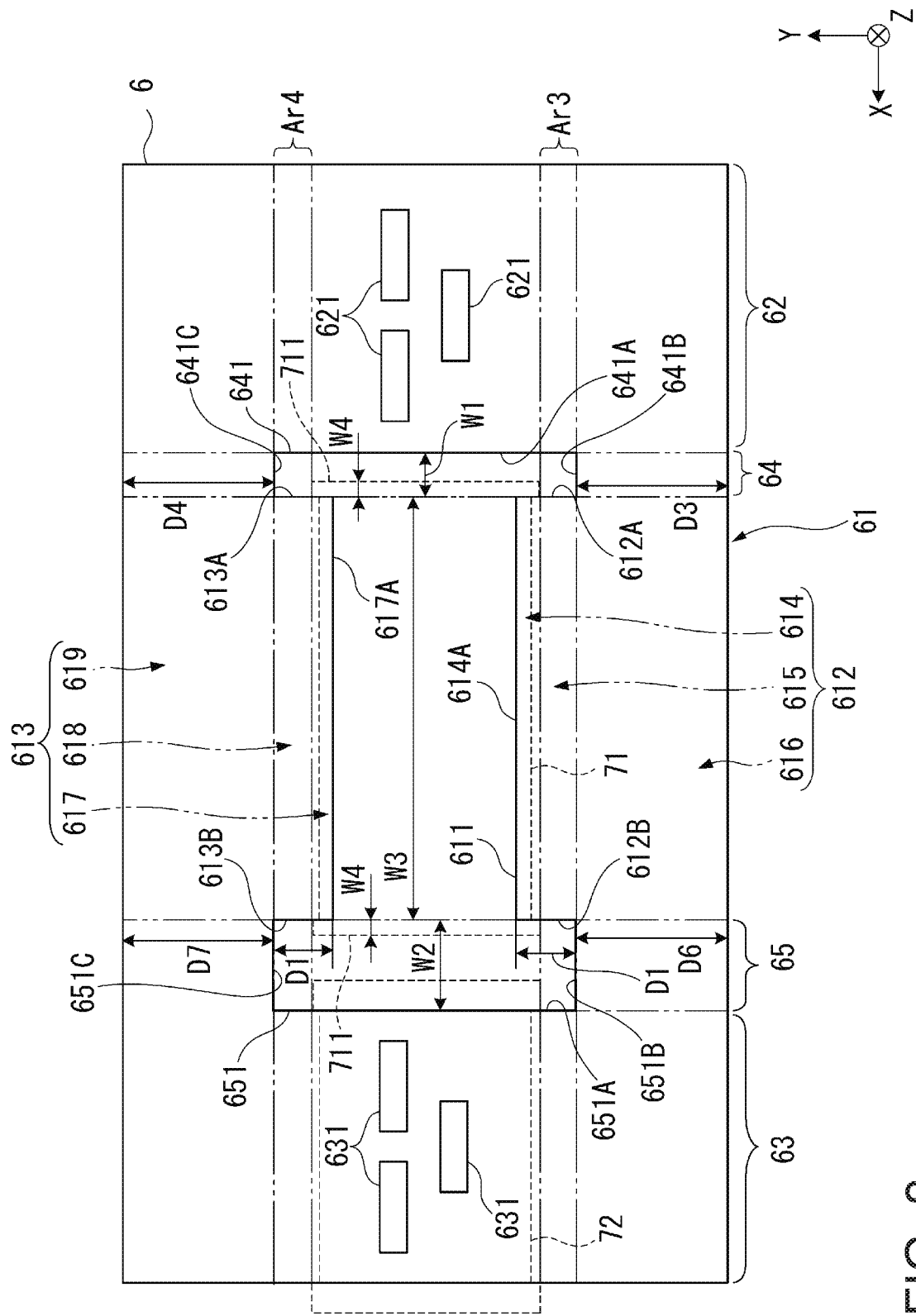
FIG. 8 is a plan view showing a schematic configuration of a surface of a flexible board of the embodiment.
Figure 9:
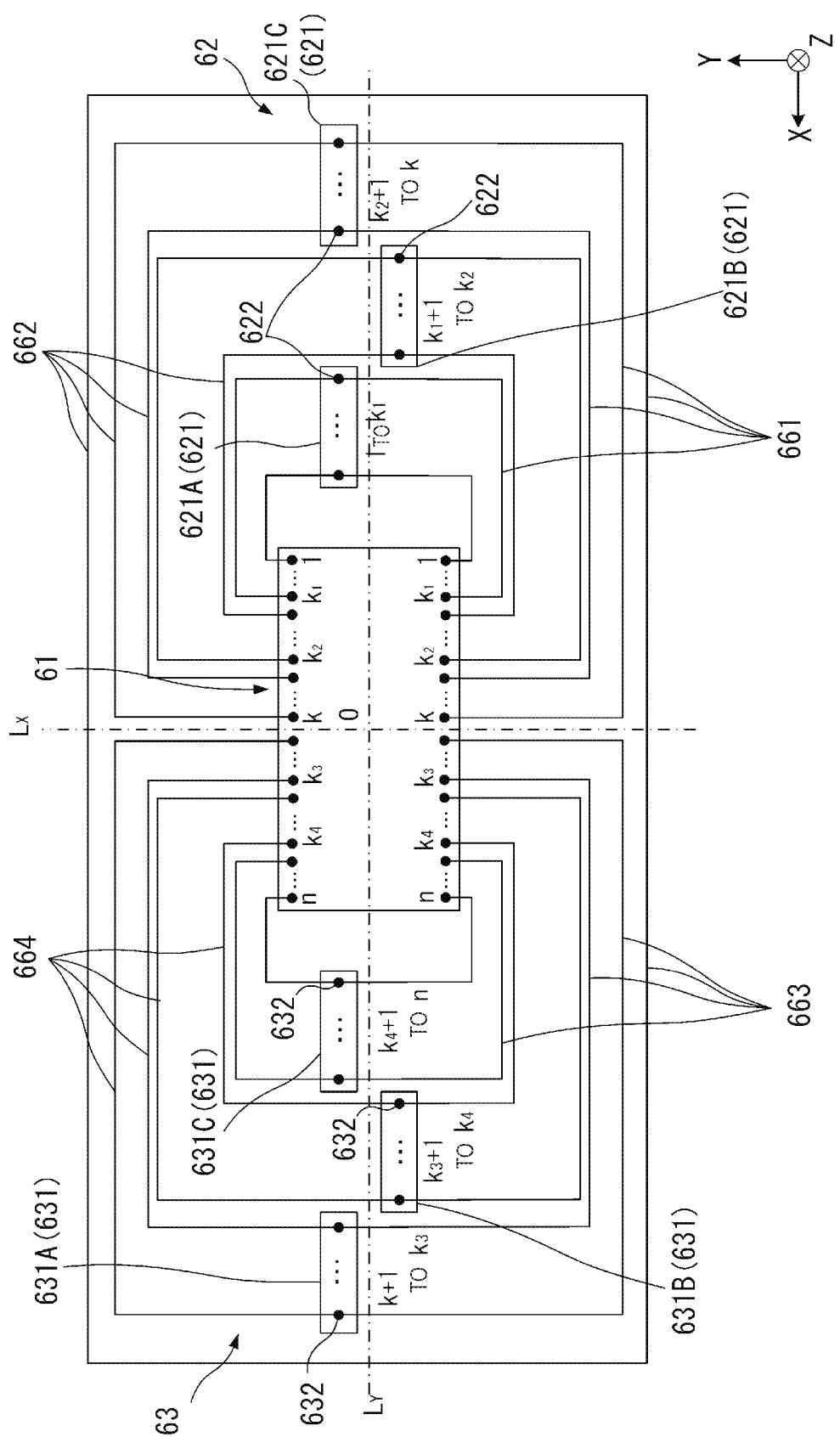
FIG. 9 is a diagram showing a wiring structure of the flexible board of the embodiment.

FIG. 8 is a plan view showing a schematic configuration of a surface of the flexible board 6 of the present embodiment. FIG. 9 is a diagram showing a wiring structure of the flexible board.

As shown in FIG. 8, the flexible board 6 is formed to have, for example, a rectangular planar shape. The flexible board 6 is divided into five regions along the X direction.

Specifically, the flexible board 6 is provided with a device connection section 61 disposed in the central area in the X direction, a first connector section 62 located on the −X side of the device connection section 61, and a second connector section 63 located on the +X side of the device connection section 61. Further, the device connection section 61 and the first connector section 62 are linked (connected) to each other via a first inflective part 64, and the device connection section 61 and the second connector section 63 are linked (connected) to each other via a second inflective part 65.

2-2-1. Description of Device Connection Section 61

The device connection section 61 is a part to which the ultrasonic device 5 is connected, and has an opening part 611 having a roughly rectangular shape corresponding to the acoustic lens 54. Further, the device connection section 61 is configured including a first wiring part 612 disposed on the −Y side of the opening part 611, and a second wiring part 613 disposed on the +Y side of the opening part 611.

The first wiring part 612 is a part in which interconnections to be connected to the first device-side terminals 531 are disposed, and is provided with a first connection part 614, a first bending part 615, and a first device stacking part 616.

The first connection part 614 has connection terminals disposed in a connection side 614A along the X direction facing the opening part 611, and connected to the respective first device-side terminals 531 along the connection side 614A.

The first bending part 615 is a part extending from the first connection part 614 toward the −Y side (in a first extending direction). Although the details will be described later, the first bending part 615 is opposed to a bending guide part 715 (see FIG. 4 and so on) provided to the first reinforcing plate 71 when bending the flexible board 6.

Further, an end edge (a first negative-side end edge 612A) on the −X side of the first connection part 614 and the first bending part 615 constitutes a part of an opening edge of a first slit 641 provided to the first inflective part 64 described later. Further, an end edge (a first positive-side end edge 612B) on the +X side of the first connection part 614 and the first bending part 615 constitutes a part of an opening edge of a second slit 651 provided to the second inflective part 65 described later.

The first device stacking part 616 is a part which overlaps the first reinforcing plate 71 when connecting the flexible board 6 to the ultrasonic device 5 supported by the first reinforcing plate 71, and bending the flexible board 6 around the first bending part 615 along the first reinforcing plate 71.

In the present embodiment, as shown in FIG. 9, the interconnections (first interconnections 661) connected to the 1-st through k-th first device-side terminals 531 out of the first device-side terminals 531 are disposed in the first device stacking part 616 so as to extend toward the first connector section 62. Meanwhile, the interconnections (third interconnections 663) connected to the (k+1)-th through n-th first device-side terminals 531 out of the first device-side terminals 531 are disposed in the first device stacking part 616 so as to extend toward the second connector section 63.

The second wiring part 613 is a part in which interconnections to be connected to the second device-side terminals 532 are disposed, and has substantially the same configuration as that of the first wiring part 612. Specifically, the second wiring part 613 is configured line symmetrically with the first wiring part 612 about a Y-central axis line $L_Y$ passing through the central point in the Y direction of the opening part 611 and parallel to the X direction.

Specifically, the second wiring part 613 is provided with a second connection part 617, a second bending part 618, and a second device stacking part 619.

The second connection part 617 has connection terminals disposed along a connection side 617A along the X direction facing the opening part 611, and connected to the respective second device-side terminals 532 along the connection side 617A.

The second bending part 618 is a part extending from the second connection part 617 toward the +Y side (in a second extending direction), and is opposed to the bending guide part 715 of the first reinforcing plate 71 described later when bending the flexible board 6.

An end edge (a second negative-side end edge 613A) on the −X side of the second connection part 617 and the second bending part 618 constitutes a part of an opening edge of the first slit 641 provided to the first inflective part 64 described later. Further, an end edge (a second positive-side end edge 613B) on the +X side of the second connection part 617 and the second bending part 618 constitutes a part of the opening edge of the second slit 651 provided to the second inflective part 65 described later.

The second device stacking part 619 is a part which overlaps the first reinforcing plate 71 together with the first device stacking part 616 when connecting the flexible board 6 to the ultrasonic device 5 fixed to the first reinforcing plate 71, and bending the second bending part 618 of the flexible board 6 along the first reinforcing plate 71.

Among the interconnections disposed in the second device stacking part 619, the interconnections (second interconnections 662) to be connected to the 1-st through k-th second device-side terminals 532 are disposed so as to extend toward the first connector section 62. Further, the interconnections (fourth interconnections 664) to be connected to the (k+1)-th through n-th second device-side terminals 532 are disposed so as to extend toward the second connector section 63.

2-2-2. Description of First Connector Section 62 and Second Connection Section 63

The first connector section 62 is provided with a plurality of connectors 621 each provided with a plurality of external connection terminals 622 (see FIG. 9), and the second connector section 63 is provided with a plurality of connectors 631 each provided with a plurality of external connection terminals 632 (see FIG. 9). As shown in FIG. 8 and FIG. 9, in the present embodiment, the first connector section 62 is provided with the three connectors 621, and the second connector section 63 is provided with the three connectors 631. Further, each of the connectors 621 is provided with the external connection terminals 622 to be connected to either of the interconnections 661, 662, and each of the connectors 631 is provided with the external connection terminals 632 to be connected to either of the interconnections 663, 664.

It should be noted that although in the present embodiment, there is shown an example in which the three connectors 621, 631 are provided, this is not a limitation, and it is also possible to provide one or two connectors 621, 631, or it is also possible to provide four or more connectors 621, 631.

Here, among the three connectors 621 provided to the first connector section 62, in the connector 621A located on the +X side, there are disposed the 1-st external connection terminal 622 through the $k_1$-th ($k_1<k$) external connection terminal 622. Further, in the connector 621A, the 1-st external connection terminal 622 is disposed at the +X side end part, and the $k_1$-th external connection terminal 622 is disposed at the −X side end part.

Among the three connectors 621 provided to the first connector section 62, in the connector 621B located in the central part in the X direction, there are disposed the $(k_1+1)$-th external connection terminal 622 through the $k_2$-th ($k_1<k_2<k$) external connection terminal 622. Further, in the connector 621B, the $(k_1+1)$-th external connection terminal 622 is disposed at the +X side end part, and the $k_2$-th external connection terminal 622 is disposed at the −X side end part.

Among the three connectors 621 provided to the first connector section 62, in the connector 621C located on the −X side, there are disposed the $(k_2+1)$-th external connection terminal 622 through the k-th external connection terminal 622. Further, in the connector 621C, the $(k_2+1)$-th external connection terminal 622 is disposed at the +X side end part, and the k-th external connection terminal 622 is disposed at the −X side end part.

Therefore, in the first connector section 62, the "i $(1\leq i\leq k)$"-th external connection terminal 622 from the +X side corresponds to the i-th external connection terminal.

Further, to the i-th external connection terminal 622, there are connected the first interconnection 661 connected to the i-th first device-side terminal 531, and the second interconnection 662 connected to the i-th second device-side terminal 532.

Here, the first interconnection 661 and the second interconnection 662 disposed in the first connector section 62 are made roughly line-symmetric about the Y-central axis line $L_Y$ similarly to the device connection section 61. In other words, the wiring length from the first device-side terminal 531 to the external connection terminal 622 in the first interconnection 661 and the wiring length from the second device-side terminal 532 to the external connection terminal 622 in the second interconnection 662 are roughly equal to each other.

On the other hand, among the three connectors 631 provided to the second connector section 63, in the connector 631A located on the +X side, there are disposed the (k+1)-th external connection terminal 632 through the $k_3$-th $(k+1\leq k_3<n)$ external connection terminal 632. Further, in the connector 631A, the (k+1)-th external connection terminal 632 is disposed at the +X side end part, and the $k_3$-th external connection terminal 632 is disposed at the −X side end part.

Among the three connectors 631 provided to the second connector section 63, in the connector 631B located in the central part in the X direction, there are disposed the $(k_3+1)$-th external connection terminal 632 through the $k_4$-th $(k_3<k_4<n)$ external connection terminal 632. Further, in the connector 631B, the $(k_3+1)$-th external connection terminal 632 is disposed at the +X side end part, and the $k_4$-th external connection terminal 632 is disposed at the −X side end part.

Among the three connectors 631 provided to the second connector section 63, in the connector 631C located on the −X side, there are disposed the $(k_4+1)$-th external connection terminal 632 through the n-th external connection terminal 632. Further, in the connector 631C, the $(k_4+1)$-th external connection terminal 632 is disposed at the +X side end part, and the n-th external connection terminal 632 is disposed at the −X side end part.

Therefore, in the second connector section 63, the "i $(k+1\leq i\leq n)$"-th external connection terminal 632 from the +X side corresponds to the i-th external connection terminal 632.

Further, to the i-th external connection terminal 632, there are connected the third interconnection 663 connected to the i-th first device-side terminal 531, and the fourth interconnection 664 connected to the i-th second device-side terminal 532.

Here, the third interconnection 663 and the fourth interconnection 664 disposed in the second connector section 63 are made roughly line-symmetric about the Y-central axis line $L_Y$ similarly to the device connection section 61. In other words, the wiring length from the first device-side terminal 531 to the external connection terminal 632 in the third interconnection 663 and the wiring length from the second device-side terminal 532 to the external connection terminal 622 in the fourth interconnection 664 are roughly equal to each other.

Here, among the first device-side terminals 531, it is preferable for the number (k) of the first device-side terminals 531 to be connected to the external connection terminals 622 of the first connector section 62, and the number (n−k) of the first device-side terminals 531 to be connected to the external connection terminals 632 of the second connector section 63 to satisfy the relationship of |(n−k)−k|/n≤0.2.

In other words, it is preferable to adopt the wiring configuration in which the difference between the number (k) of the first device-side terminals 531 to be connected to the external connection terminals 622 and the number (n−k) of the first device-side terminals 531 to be connected to the external connection terminals 632 is equal to or lower than 20% of the total number (n) of the first device-side terminals 531. Further, it is more preferable that n is an even number, and k=n/2 is assumed.

Figure 10:
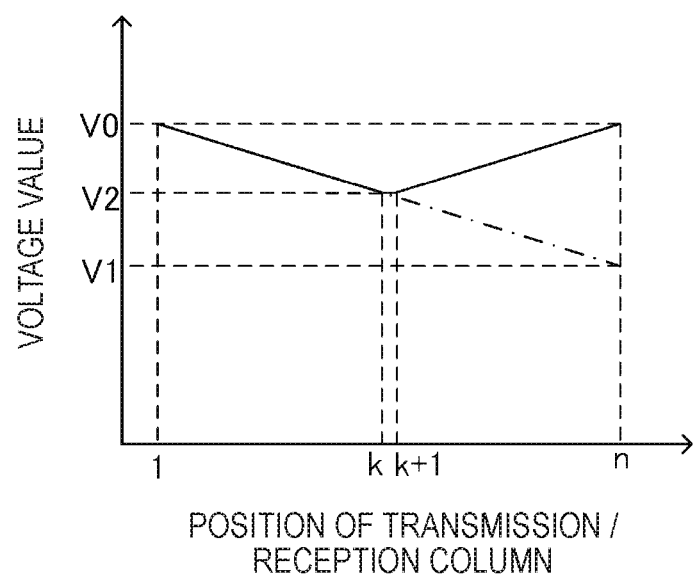
FIG. 10 is a diagram showing a voltage value of a drive voltage to be applied to each of transmission/reception columns of an ultrasonic device.

FIG. 10 is a diagram showing a voltage value of a drive voltage to be applied to each of the transmission/reception columns Ch. In FIG. 10, the dashed-dotted line represents the voltage value in the case of using the flexible board (related art example) having just one connector section with respect to the device connection section, and the solid line represents the voltage value in the present embodiment.

As shown in FIG. 10, in the past, the device-side terminals located close to the connector section are connected to the external connection terminals located on the device connection section side of the connector section, and the device-side terminals located farther from the connector section are connected to the external connection terminals located farther from the device connection section of the connector section. Therefore, as the device-side terminal is located farther from the connector section, the length of the interconnection also increases, and due to the influence of the voltage drop, the voltage value of the drive voltage applied to each of the transmission/reception columns Ch connected to the device-side terminals also drops.

In contrast, in the present embodiment, there are provided the first connector section 62 and the second connector section 63 as described above, and the interconnections 661, 662 are provided to the connector section 62, and the interconnections 663, 664 are provided to the connector section 63, wherein the numbers of the interconnections 661, 662, 663, and 664 are the same. Further, in the present embodiment, the first interconnections 661 and the third interconnections 663 are made roughly line-symmetric about an X-central axis line $L_X$ passing through the center of the ultrasonic device 5 and parallel to the Y direction, and the second interconnections 662 and the fourth interconnections 664 are made roughly line-symmetric about the X-central axis line $L_X$. Therefore, the first interconnection 661 connected to the i-th first device-side terminal 531, the second interconnection 662 connected to the i-th second device-side terminal 532, the third interconnection 663 connected to the (i+n/2)-th first device-side terminal 531, and the fourth interconnection 664 connected to the (i+n/2)-th second device-side terminal 532 become roughly the same in length, and as shown in FIG. 10, the influence of the voltage drop is suppressed.

2-2-3. Configuration of First Inflective Part 64 and Second Inflective Part 65

As shown in FIG. 8, the first inflective part 64 is disposed between the device connection section 61 and the first connector section 62, and links the first connector section 62 to the device connection section 61 in a bendable manner. Similarly, the second inflective part 65 is disposed between the device connection section 61 and the second connector section 63, and links the second connector section 63 to the device connection section 61 in a bendable manner.

The first inflective part 64 has the first slit 641 linked to the opening part 611 provided to the device connection section 61.

As shown in FIG. 8, the first slit 641 is an opening elongated along the Y direction, and includes the first negative-side end edge 612A, which is the end edge on the −X side of the first connection part 614 and the first bending part 615, and the second negative-side end edge 613A, which is the end edge on the −X side of the second connection part 617 and the second bending part 618 as a part of the opening edge on the +X side. In the present embodiment, the first negative-side end edge 612A and the second negative-side end edge 613A are located on a straight line along the Y direction. The opening edge opposed to the first negative-side end edge 612A and the second negative-side end edge 613A of the first slit 641 forms a first opposed edge 641A shaped like a straight line parallel to the Y direction.

Further, the end edge (a first slit end edge 641B) on the −Y side of the first slit 641 links the −Y side end parts of the first opposed edge 641A and the first negative-side end edge 612A to each other, and the end edge (a first slit end edge 641C) on the +Y side of the first slit 641 links the +Y side end parts of the first opposed edge 641A and the second negative-side end edge 613A to each other. The first slit end edge 641B is disposed at a position shifted from the first connection part 614 toward the −Y side as much as a dimension D1. Similarly, the first slit end edge 641C is disposed at a position shifted from the second connection part 617 toward the +Y side as much as the dimension D1.

Here, the dimension D1 is set to a dimension larger than a distance from the wiring board 53 to a first side 71A (see FIG. 11) of the first reinforcing plate 71 in the case of connecting the flexible board 6 to the ultrasonic device 5 supported by the first reinforcing plate 71 (see FIG. 11) described later.

The second inflective part 65 has the second slit 651 linked to the opening part 611 provided to the device connection section 61.

The second slit 651 has roughly the same configuration as that of the first slit 641, and is connected to the opening part 611, including the first positive-side end edge 612B and the second positive-side end edge 613B as a part of the opening edge on the −X side. The opening edge opposed to the first positive-side end edge 612B and the second positive-side end edge 613B of the second slit 651 forms a second opposed edge 651A shaped like a straight line parallel to the Y direction.

Further, the end edge (a second slit end edge 651B) on the −Y side of the second slit 651 links the −Y side end parts of the second opposed edge 651A and the first positive-side end edge 612B to each other, and the end edge (a second slit end edge 651C) on the +Y side of the second slit 651 links the +Y side end parts of the second opposed edge 651A and the second positive-side end edge 613B to each other. The second slit end edge 651B is disposed at a position shifted from the first connection part 614 toward the −Y side as much as the dimension D1, and the second slit end edge 651C is disposed at a position shifted from the second connection part 617 toward the +Y side as much as the dimension D1.

Here, the dimension from the first negative-side end edge 612A to the first opposed edge 641A and the dimension from the second negative-side end edge 613A to the first opposed edge 641A are the same as each other, and are defined as a width dimension W1 in the X direction in the first slit 641. Further, the dimension from the first positive-side end edge 612B to the second opposed edge 651A and the dimension from the second positive-side end edge 613B to the second opposed edge 651A are the same as each other, and are defined as a width dimension W2 in the X direction in the second slit 651. In the present embodiment, the width dimension W1 of the first slit 641 and the width dimension W2 of the second slit 651 are different from each other, and satisfy W1<W2.

2-3. Configuration of First Reinforcing Plate 71 and Second Reinforcing Plate 72

2-3-1. Configuration of First Reinforcing Plate 71

Figure 11:
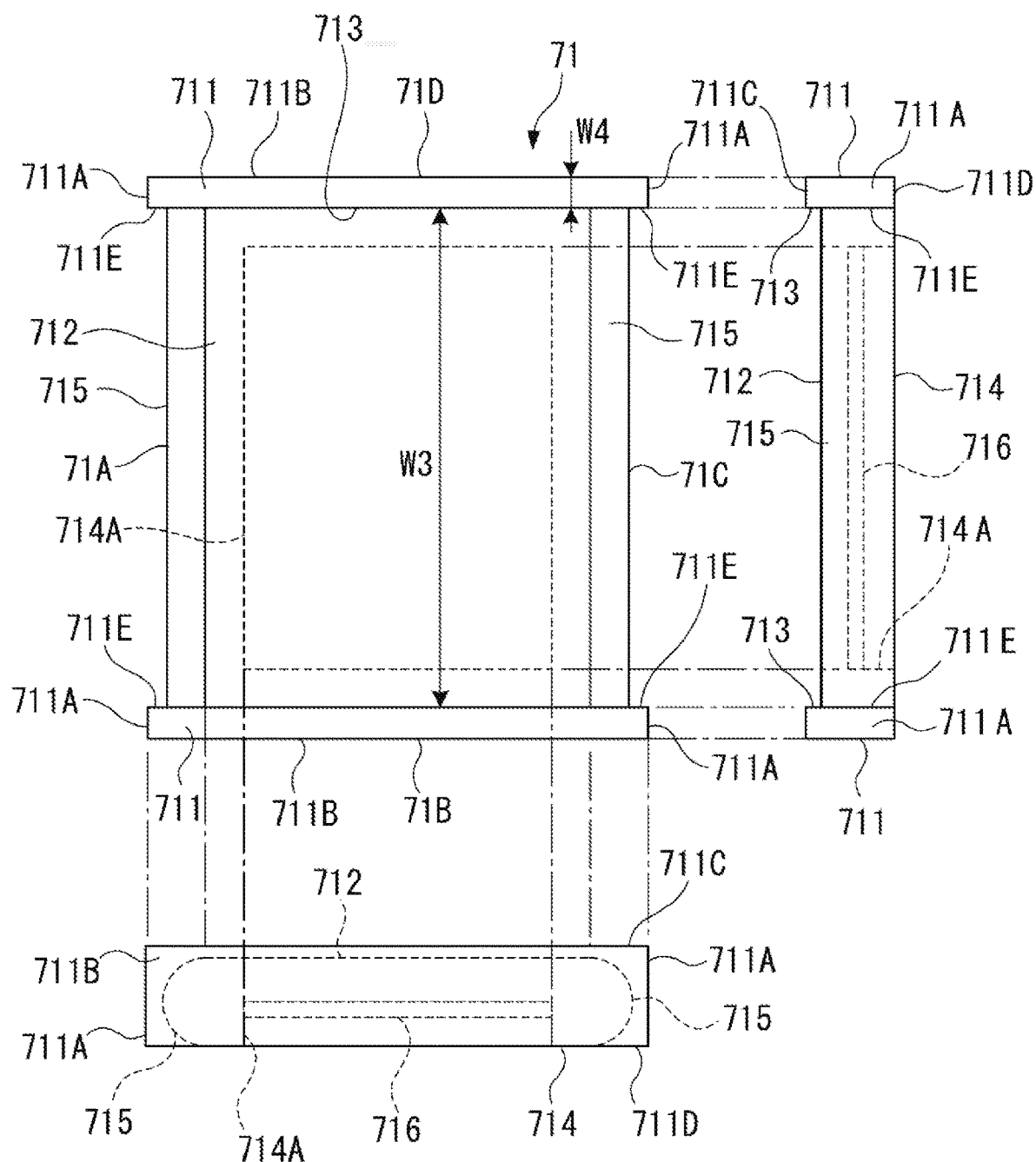
FIG. 11 is a plan view, a front view, and a side view of a first reinforcing plate of the embodiment.

FIG. 11 is a plan view, a front view, and a side view of a first reinforcing plate 71.

The first reinforcing plate 71 supports the ultrasonic device 5, and is fixed to the housing 21. Further, the first reinforcing plate 71 is formed of a resin material in order to prevent short circuit of the interconnections of the flexible board 6 when the first reinforcing plate 71 has contact with the flexible board 6 connected to the ultrasonic device 5.

As shown in FIG. 11, the first reinforcing plate 71 has, for example, a roughly rectangular shape in a plan view viewed from the substrate thickness direction, and is provided with a first side 71A (−Y side) and a third side 71C (+Y side) parallel to the X direction, and a second side 71B (−X side) and a fourth side 71D (+X side) parallel to the Y direction.

The first reinforcing plate 71 is provided with positioning blocks 711 along the second side 71B and the fourth side 71D, respectively. Specifically, there are disposed the positioning block 711 located in an area from a corner part between the first side 71A and the second side 71B through a corner part between the second side 71B and the third side 71C, and the positioning block 711 located in an area from a corner part between the third side 71C and the fourth side 71D through a corner part between the fourth side 71D and the first side 71A. These positioning blocks 711 correspond to reference corner parts, and each function as a positioning part when fixing the first reinforcing plate 71 to the housing 21.

Each of the positioning blocks 711 is provided with first reference surfaces 711A parallel to the X direction, a second reference surface 711B parallel to the Y direction, and a third reference surface 711C and a fourth reference surface 711D crossing the first reference surfaces 711A and the second reference surface 711B.

Specifically, the first reference surfaces 711A are ±Y side end surfaces of the positioning block 711, and are planes parallel to the X-Z plane.

The second reference surface 711B is a −X side end surface in the positioning block 711 located on the second side 71B side, and a +X side end surface in the positioning block 711 located on the fourth side 71D side, and is a plane parallel to the Y-Z plane.

The third reference surface 711C is a +Z side end surface of each of the positioning blocks 711, and has contact with the housing 21. The third reference surface 711C is located on the +Z side with respect to the surface (a fixation surface 712) on the +Z side of the central part of the first reinforcing plate 71. Thus, a step 713 is disposed between the third reference surface 711C and the fixation surface 712, and due to the step 713, the ±X side end surfaces of the ultrasonic device 5 are positioned. Here, it is preferable for the height dimension (the dimension in the Z direction) of the step 713 to be equal to or larger than at least the thickness dimension of the flexible board 6.

The fourth reference surface 711D is a surface forming a reverse surface with respect to the third reference surface 711C, and when housing the ultrasonic device unit 4 in the housing 21, the second reinforcing plate 72 described later is mounted on the fourth reference surface 711D.

It should be noted that in the present embodiment, the fourth reference surface 711D is disposed in the same plane as the reverse surface 714 as shown in FIG. 11.

Further, the width dimension W4 in the X direction of the positioning block 711 is smaller than the width dimension W1 of the first slit 641 and the width dimension W2 of the second slit 651 (see FIG. 8).

Further, in each of the positioning blocks 711, a surface (a surface on the opposite side to the second reference surface 711B) crossing the first side 71A and the third side 71C forms a guide surface 711E. The guide surface 711E is a surface parallel to the Y-Z plane, and has contact with the end edges 612A, 612B, 613A, and 613B when bending the first bending part 615 and the second bending part 618 of the flexible board 6 along the bending guide part 715.

Further, on the ±Y sides of the fixation surface of the first reinforcing plate 71, there are disposed the bending guide parts 715 along the first side 71A and the third side 71C, respectively. The Y-Z cross-section of the bending guide part 715 has an arc-like shape protruding in a direction of getting away from the fixation surface 712, and continuous with the fixation surface 712 and the reverse surface 714.

Here, the tip of the protrusion of the bending guide part 715 is located on the fixation surface 712 side of the first reference surface 711A. Specifically, the first reference surfaces 711A located on the both end sides of the first side 71A are located at a position shifted from the −Y side end part of the bending guide part 715 extending along the first side 71A toward the −Y side as much as an amount at least equal to or larger than the thickness of the flexible board 6. Further, the first reference surfaces 711A located on the both end sides of the third side 71C are located at a position shifted from the +Y side end part of the bending guide part 715 extending along the third side 71C toward the +Y side as much as an amount at least equal to or larger than the thickness of the flexible board 6.

Further, the distance along the X direction between a pair of guide surfaces 711E opposed to each other across the first side 71A is roughly the same as the width dimension W3 in the X direction of the first connection part 614 and the first bending part 615 of the flexible board 6.

Incidentally, the first reinforcing plate 71 is formed of the resin material as described above, and is therefore lower in strength compared to the case of being formed of, for example, metal. Therefore, in order to increase the substrate strength, the first reinforcing plate 71 is provided with a recessed part 714A disposed on the reverse surface 714, and a metal plate 716 is disposed in the recessed part 714A. The metal plate 716 is disposed on the bottom surface of the recessed part 714A, and does not protrude outward (the −Z side) from the reverse surface 714. Thus, even when bending the flexible board 6 toward the reverse surface 714 side of the first reinforcing plate 71, the flexible board 6 and the metal plate 716 do not interfere with each other.

2-3-2. Configuration of Second Reinforcing Plate 72

As shown in FIG. 3 and FIG. 4, the second reinforcing plate 72 supports the second connector section 63.

Figure 12:
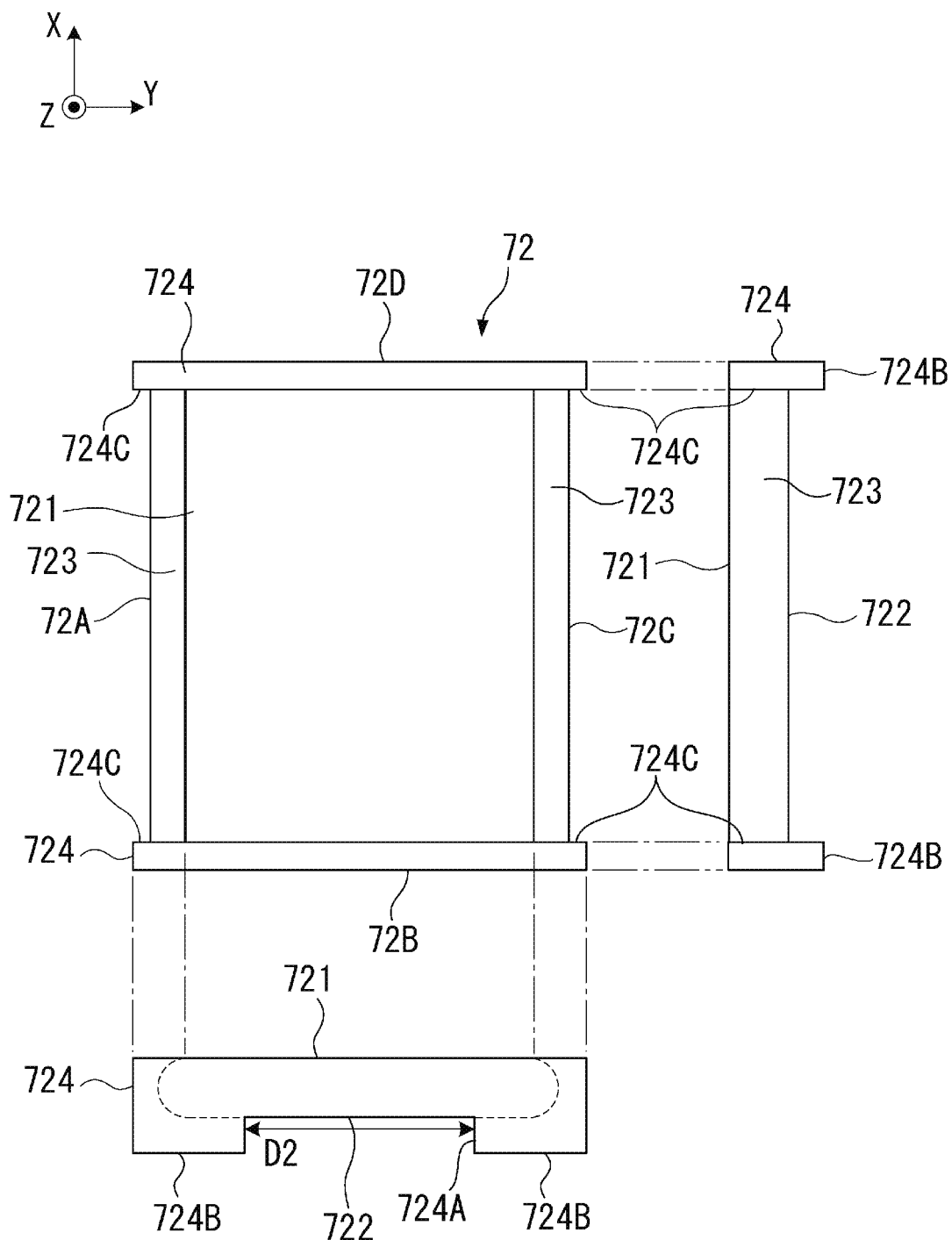
FIG. 12 is a plan view, a front view, and a side view of a second reinforcing plate of the embodiment.

FIG. 12 is a plan view, a front view, and a side view of the second reinforcing plate 72.

As shown in FIG. 12, the second reinforcing plate 72 has a roughly rectangular shape having a fifth side 72A, a sixth side 72B, a seventh side 72C, and an eighth side 72D in a planar view viewed from the plate thickness direction similarly to the first reinforcing plate 71.

The second reinforcing plate 72 is provided with a connector support surface 721 with which the central part (an area where the connectors 631 are disposed) of the second connector section 63 has contact, and a reverse surface 722 on the opposite side to the connector support surface 721. Further, the second reinforcing plate 72 is provided with second bending guide parts 723 each curved to have an arc-like shape disposed respectively in the fifth side 72A and the seventh side 72C extending along the X direction similarly to the first reinforcing plate 71.

Further, the second reinforcing plate 72 is provided with second positioning blocks 724 respectively disposed along the sixth side 72B and the eighth side 72D located on the ±X sides similarly to the first reinforcing plate 71.

The second positioning blocks 724 are each provided with a recessed part 724A on a surface on the opposite side to the connector support surface 721. The recessed part 724A forms a configuration space for the first inflective part 64 and the second inflective part 65 of the flexible board 6. Specifically, the width dimension D2 in the Y direction of the recessed part 724A of the second positioning block 724 located on the −X side is equal to or larger than the dimension D3 (see FIG. 8) from the −Y side end edge of the first inflective part 64 to the first slit end edge 641B, and the dimension D4 (see FIG. 8) from the +Y side end edge of the first inflective part 64 to the first slit end edge 641C, and it is preferable to fulfill D2=D3=D4.

Further, although not shown in the drawings, the width dimension in the Y direction of the recessed part 724A of the second positioning block 724 located on the +X side is equal to or larger than the dimension D6 (see FIG. 8) from the −Y side end edge of the second inflective part 65 to the second slit end edge 651B, and the dimension D7 (see FIG. 8) from the +Y side end edge of the second inflective part 65 to the second slit end edge 651C, and is preferably equal to the dimensions D6 and D7.

Further, on a surface on the opposite side to the connector support surface 721 of the second positioning block 724, there are disposed mount surfaces 724B across the recessed part 724A from each other. The mount surfaces 724B are mounted on the fourth reference surface 711D when storing the second reinforcing plate 72 in the housing 21.

In the present embodiment, the mount surfaces 724B are located on the −Z side (+Z side when stored in the housing 21) of the reverse surface 722. Thus, when mounting the mount surfaces 724B on the fourth reference surface 711D, between the reverse surface 714 of the first reinforcing plate 71 and the reverse surface 722 of the second reinforcing plate 72, there is formed a space at least equal to or larger than the configuration space for the flexible board 6 that is folded multiple times and the connectors 621 of the first connector section 62.

The surface on the fifth side 72A side and on the seventh side 72C side of each of the second positioning blocks 724 forms a second guide surface 724C for guiding the second opposed edge 651A of the second slit 651 of the flexible board 6, and an outer peripheral edge on the −X side of the flexible board 6.

2-4. Configuration of Housing 21

As shown in FIG. 2, the housing 21 is provided with a storage part 211 and a lid part 212.

As shown in FIG. 3 and FIG. 4, the storage part 211 is a vessel-like member for storing the ultrasonic device unit 4, and has a sensor window 211B in a bottom part 211A, wherein the acoustic lens 54 of the ultrasonic device 5 is exposed to the outside from the sensor window 211B.

Further, in the bottom part 211A of the storage part 211, there is disposed a device installation part 213 so as to surround the sensor window 211B. The device installation part 213 is formed to have a frame-like shape rising from the bottom part 211A so that the four corners of the first reinforcing plate 71 are fitted into the device installation part 213.

2-5. Storage of Ultrasonic Device Unit 4 into Housing 21

In such an ultrasonic probe 2 as described above, firstly, the ultrasonic device 5 is fixed to the fixation surface 712 of the first reinforcing plate 71.

Then, the first connection part 614 of the flexible board 6 is connected to the −X side of the wiring board 53 of the ultrasonic device 5. Thus, the connection terminals of the first connection part 614 and the first device-side terminals 531 are electrically connected to each other, respectively. Further, the second connection part 617 is connected to the +X side of the wiring board 53 of the ultrasonic device 5. Thus, the connection terminals of the second connection part 617 and the second device-side terminals 532 are electrically connected to each other, respectively.

On this occasion, the first negative-side end edge 612A of the flexible board 6 is made to have contact with (be guided by) the guide surface 711E located on the −X side of the first side 71A, and the first positive-side end edge 612B is made to have contact with (be guided by) the guide surface 711E located on the +X side of the first side 71A. Further, the second negative-side end edge 613A of the flexible board 6 is made to have contact with (be guided by) the guide surface 711E located on the −X side of the third side 71C, and the second positive-side end edge 613B is made to have contact with (be guided by) the guide surface 711E located on the +X side of the third side 71C.

Figure 13:
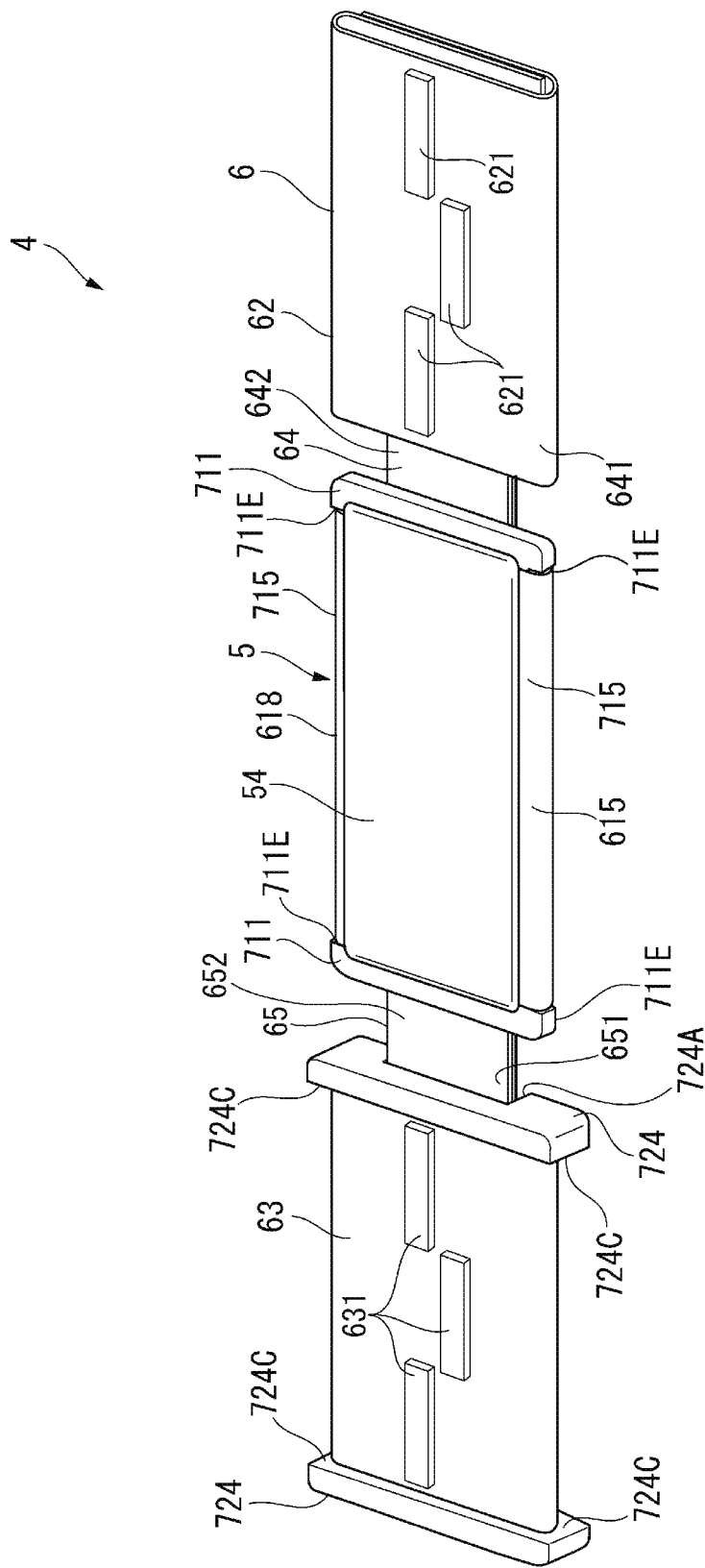
FIG. 13 is a perspective view of the case in which the flexible board is curved along an X direction in the embodiment.

FIG. 13 is a perspective view of the case in which the flexible board 6 is curved along the X direction in the present embodiment.

Subsequently, the flexible board 6 is curved in a first bending area Ar3 (see FIG. 8) including the first bending part 615 parallel to the X direction to fold back the end edge on the −Y side of the flexible board 6 toward the +Y side. Further, the flexible board 6 is curved in a second bending area Ar4 (see FIG. 8) including the second bending part 618 parallel to the X direction to fold back the end edge on the +Y side of the flexible board 6 toward the −Y side. It should be noted that either one of the first bending area Ar3 and the second bending area Ar4 can be folded back first.

Here, as shown in FIG. 13, the end edges (the first negative-side end edge 612A and the first positive-side end edge 612B) of the ±X sides of the first bending part 615 and the end edges (the second negative-side end edge 613A and the second positive-side end edge 613B) on the ±X sides of the second bending part 618 are guided by the guide surfaces 711E to be curved along the arcs of the bending guide parts 715.

Thus, in the flexible board 6, the first bending area Ar3 can be bent along (in parallel to the X direction) the first side 71A of the first reinforcing plate 71, and thus, the first device stacking part 616 is stacked on the reverse surface 714 side of the first reinforcing plate 71 so as to overlap the first reinforcing plate 71. Further, the second bending area Ar4 can be bent along (in parallel to the X direction) the third side 71C of the first reinforcing plate 71, and thus, the second device stacking part 619 is stacked on the reverse surface 714 side of the first reinforcing plate 71 so as to overlap the first reinforcing plate 71.

Similarly, in each of the first connector section 62, the first inflective part 64 and the second inflective part 65, an area located on the −Y side of the first bending area Ar3 is made to overlap a central area (an area where the connectors 621, 632 are disposed) between the first bending area Ar3 and the second bending area Ar4. Further, in each of the first connector section 62, the first inflective part 64 and the second inflective part 65, an area located on the +Y side of the second bending area Ar4 is made to overlap the central area.

Further, the first bending area Ar3 and the second bending area Ar4 of the second connector section 63 are guided by the second guide surfaces 724C to be curved along the second bending guide parts 723 of the second reinforcing plate 72, and thus, an area located on the −Y side of the first bending area Ar3 of the second connector section 63 and an area located on the +Y side of the second bending area Ar4 are made to overlap the reverse surface of the second reinforcing plate 72.

As described above, when curving the flexible board 6, the first slit end edges 641B, 641C of the first slit 641 and the second slit end edges 651B, 651C of the second slit 651 move to the positions to be overlapped with the central area. Therefore, even in the case in which the flexible board 6 is folded back in the first bending area Ar3 and the second bending area Ar4 to be deformed to have a roughly cylindrical shape, in each of the first inflective part 64 and the second inflective part 65, there is formed a shape in which the flexible board 6 is disposed only on the reverse surface 714 side of the first reinforcing plate 71. Therefore, the first inflective part 64 and the second inflective part 65 are easily bent toward the reverse surface 714 side of the first reinforcing plate 71.

Further, in the present embodiment, the width dimension W1 in the X direction of the first slit 641 in the first inflective part 64 is smaller than the width dimension W2 in the X direction of the second slit in the second inflective part 65. Therefore, when bending the first inflective part 64 and second inflective part 65, the first inflective part 64 is bent first, and then the first connector section 62 is overlapped with the first reinforcing plate 71. Here, since the X-width dimension of the first connector section 62 is smaller than the X-width dimension of the first reinforcing plate 71, the first connector section 62 does not project toward the second inflective part 65, and does not hinder bending of the second inflective part 65.

Further, by bending the first inflective part 64 toward the reverse surface 714 side of the first reinforcing plate 71, the connectors 621 in the first connector section 62 project toward the −Z side.

Then, the first reinforcing plate 71 is fixed to the storage part 211 of the housing 21.

Specifically, as shown in FIG. 3 and FIG. 4, the first reference surfaces 711A and the second reference surfaces 711B of the positioning blocks 711 provided to the first reinforcing plate 71 are made to have contact with, and then fitted into, the device installation part 213 provided to the housing 21. Thus, the third reference surfaces 711C of the first reinforcing plate 71 have contact with the bottom part 211A of the housing 21, and the acoustic lens 54 of the ultrasonic device 5 projects from the sensor window 211B.

Further, on this occasion, each of the connectors 621 in the first connector section 62 is exposed on the opposite side to the bottom part 211A of the storage part 211. Then, the terminals disposed on the tip of the cable 3 are connected to the connectors 621.

Figure 14:
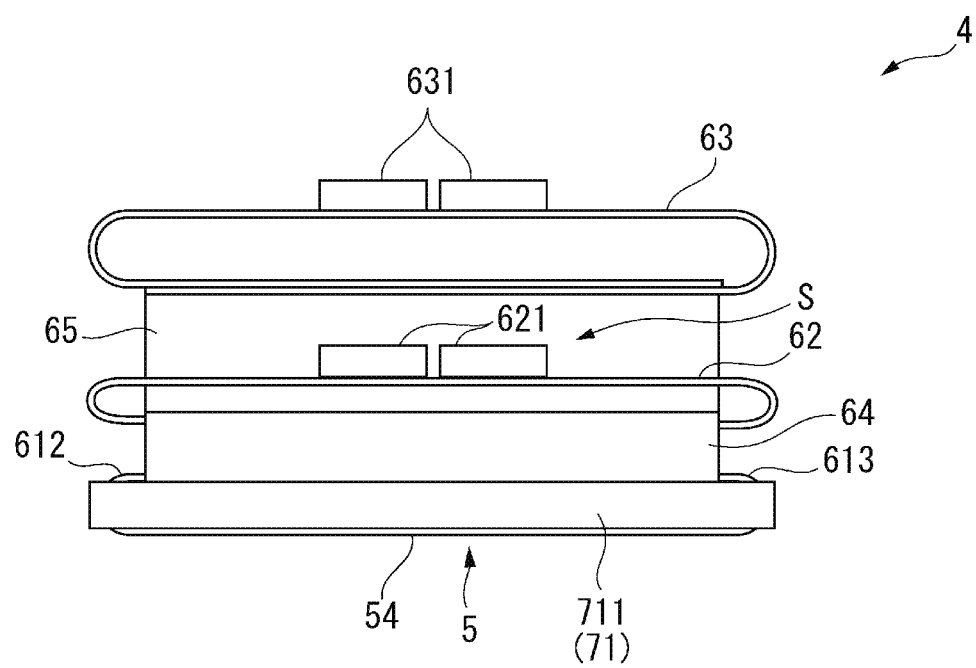
FIG. 14 is a side view of an ultrasonic device unit according to the embodiment viewed from a first inflective part side.
Figure 15:
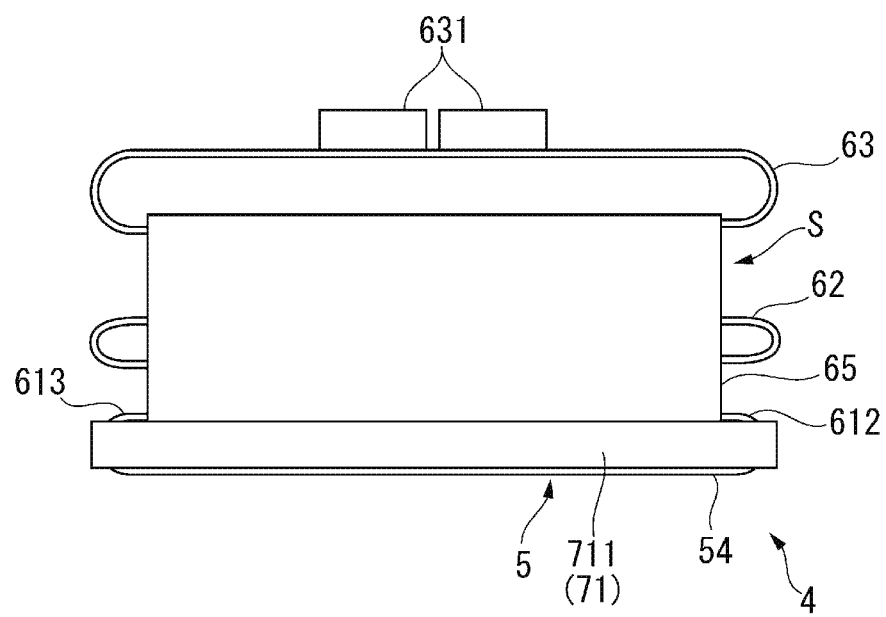
FIG. 15 is a side view of the ultrasonic device unit according to the embodiment viewed from a second inflective part side.

FIG. 14 is a side view of the ultrasonic device unit 4 housed in the housing 21 viewed from the first inflective part 64 side, and FIG. 15 is a side view viewed from the second inflective part 65 side. It should be noted that the illustration of the second reinforcing plate 72 is omitted in FIG. 14 and FIG. 15.

Subsequently, the second inflective part 65 is bent to overlap the second reinforcing plate 72 which supports the second connector section 63 with the first reinforcing plate 71. Thus, the mount surfaces 724B of the second positioning blocks 724 of the second reinforcing plate 72 are mounted on the fourth reference surfaces 711D of the positioning blocks 711 of the first reinforcing plate 71.

On this occasion, since the width dimension W2 of the second slit 651 in the second inflective part 65 satisfies W2>W1, the second connector section 63 does not interfere with the first connector section 62, and the first inflective part 64 and the second inflective part 65 do not project outside as shown in FIG. 14 and FIG. 15, and therefore, miniaturization of the flexible board 6 can be advanced.

Further, when mounting the mount surfaces 724B of the second reinforcing plate 72 on the fourth reference surfaces 711D of the first reinforcing plate 71, the configuration space S for disposing the flexible board 6 and the first connector section 62 is formed between the reverse surface 714 of the first reinforcing plate 71 and the reverse surface 722 of the second reinforcing plate 72. In the configuration space S, there are disposed the first device stacking part 616, the second device stacking part 619, the first connector section 62 bent to be triply overlapped, the second connector section 63 bent toward the reverse surface 722 side of the second reinforcing plate 72 to be doubly overlapped, the connectors in the first connector section 62, and the terminals of the cable 3 to be connected to the connectors (the illustration of the cable 3 is omitted in FIG. 2 and FIG. 3).

Further, since the connectors 631 of the second connector section 63 supported by the second reinforcing plate 72 are exposed on the −Z side, the terminals provided to the tip of the cable 3 are connected to the connectors 631. Subsequently, the lid part 212 is fixed to the storage part 211, and the space between the sensor window 211B and the acoustic lens 54 is sealed with a resin material such as silicone resin, and thus, the ultrasonic probe 2 is assembled.

3. Functions and Advantages of Present Embodiment

In the ultrasonic device unit 4 according to the present embodiment, the ultrasonic device 5 has the 1-st through n-th device-side terminals (the first device-side terminals 531 and the second device-side terminals 532) corresponding respectively to the 1-st through n-th transmission/reception columns Ch. Further, flexible board 6 is provided with the device connection section 61, the first connector section 62, and the second connector section 63 to be connected to the respective device-side terminals of the ultrasonic device 5. Further, the 1-st through k-th device-side terminals are connected to the external connection terminals 622 provided to the connecters 621 of the first connector section 62, and the (k+1)-th through n-th device-side terminals are connected to the external connection terminals 632 provided to the connectors 631 of the second connector section 63.

In such a configuration, since it is possible to distribute the interconnections 661, 662, 663, 664 to the first connector section 62 and the second connector section 63, the length of each of the interconnections 661, 662, 663, 664 can be made shorter compared to the case in which, for example, one connector is provided alone to the flexible board, and thus, the influence of the voltage drop can be suppressed as shown in FIG. 10. Thus, since the influence on the transmission/reception efficiency of the ultrasonic wave in the ultrasonic device 5 can also be suppressed, it is possible to perform the ultrasonic measurement high in accuracy with the ultrasonic probe 2, and thus, it is possible to perform highly accurate processes (e.g., formation of an internal tomographic image) based on the ultrasonic measurement result in the ultrasonic measurement apparatus 1.

In the ultrasonic device 5 according to the present embodiment, the plurality of ultrasonic transducers Tr arranged in the Y direction constitutes one transmission/reception column Ch, and the plurality of transmission/reception columns Ch is arranged in the X direction. Further, the −Y side end part of each of the transmission/reception columns Ch is connected to the first device-side terminal 531, and the +Y side end part thereof is connected to the second device-side terminal 532. Further, in the flexible board 6, these first device-side terminal 531 and the second device-side terminal 532 are connected to the same external connection terminal 622 (or the external connection terminal 632). Therefore, it is possible to input the same drive signal to the both ends of the transmission/reception column Ch, and thus, it is possible to reduce the influence of the voltage drop in the transmission/reception column Ch.

Further, the first interconnections 661 and the third interconnections 663 for connecting the first device-side terminals 531 and the external connection terminals 622, 632 to each other are roughly symmetrical with the second interconnections 662 and the fourth interconnections 664 for connecting the second device-side terminals 532 and the external connection terminals 622, 632 to each other, respectively. Therefore, even if the voltage drop occurs in each of the interconnections 661, 662, 663, and 664, it is possible to suppress the disadvantage that the intensities of the ultrasonic waves which are made to be output from the ultrasonic device 5 become non-uniform.

In the present embodiment, in the flexible board 6, there are arranged the first connector section 62, the device connecting section 61, and the second connector section 63 in this order along the X direction.

In such a configuration, the first interconnections 661 and the second interconnections 662 extending from the device connection section 61 toward the first connector section 62, and the third interconnections 663 and the fourth interconnections 664 extending from the device connection section 61 toward the second connector section 63 can be formed roughly line-symmetrically with each other. Therefore, even in the case in which the voltage drop occurs, the transmission/reception efficiency of the ultrasonic wave output from the first connector section 62 side in the ultrasonic device 5 and the transmission/reception efficiency of the ultrasonic wave output from the second connector section 63 side become roughly equal to each other. Therefore, it is prevented that the transmission/reception efficiency of the ultrasonic wave significantly lowers in a part of the ultrasonic device, and the appropriate transmission/reception process of the ultrasonic wave can be performed.

In the present embodiment, the number of the first interconnections 661 and the second interconnections 662 extending from the device connection section 61 toward the first connector section 62, and the number of the third interconnections 663 and the fourth interconnections 664 extending from the device connection section 61 toward the second connector section 63 are the same as each other. Therefore, between the ultrasonic transducers Tr connected to the first connector section 62 and the ultrasonic transducers Tr connected to the second connector section 63, the influence of the voltage drop can be made roughly the same, and thus, the transmission/reception efficiency of the ultrasonic wave in the ultrasonic device 5 can be equalized.

Modified Examples

It should be noted that the invention is not limited to the embodiment and the modified examples described above, but includes modifications and improvements within a range in which the advantages of the invention can be achieved, and configurations which can be obtained by arbitrary combinations of the embodiment and modified examples, and so on.

Although in the embodiment described above, there is illustrated the configuration in which the ultrasonic device 5 is provided with the first device-side terminals 531 and the second device-side terminals 532, it is also possible to adopt a configuration provided with only either one of the device-side terminals. For example, in the case in which the second device-side terminals 532 are not provided, there is obtained a configuration in which the first interconnections 661 for connecting the first device-side terminals 531 and the first connector section 62 to each other, and the third interconnections 663 for connecting the first device-side terminals 531 and the second connector section 63 to each other. Also in this case, by configuring the first interconnections 661 and the third interconnections 663, for example, line-symmetrically with each other, it is possible to reduce the influence of the voltage drop to thereby improve the transmission/reception efficiency of the ultrasonic wave in the ultrasonic device 5.

Although in the embodiment described above, there is described the example in which the number k of the first interconnections 661 (the second interconnections 662) extending from the device connection section 61 to the first connector section 62 is set to k=n/2, it is sufficient to fulfill |(n−k)−k|/n≤0.2 as described above.

In other words, if the difference between the number of the interconnections to the first connector section 62 and the number of the interconnections to the second connector section 63 is equal to or lower than 20% of the total number of the interconnections, it is possible to sufficiently reduce the influence of the voltage drop.

Further, in the embodiment described above, there is shown the example in which the first connector section 62, the device connection section 61, and the second connector section 63 are disposed along the X direction, but this is not a limitation.

For example, it is also possible to adopt a configuration in which the first connector section 62 is disposed on the +X side of the device connection section 61, and the second connector section 63 is dispose on the +Y side of the device connection section 61. Also in this case, by making the length of the interconnections extending toward the first connector section 62 and the length of the interconnections extending toward the second connector section 63 equal to each other, it is possible to suppress the influence of the voltage drop.

In the embodiment described above, there is described the example in which the first interconnections 661 and the second interconnections 662 become roughly line-symmetric with each other, and the first interconnections 661 and the third interconnections 663 become roughly line-symmetric with each other, this is not a limitation. It is not required for the interconnections 661, 662, 663, and 664 to be formed so as to have symmetrical shapes with each other. For example, by making the interconnections roughly equal in length dimension to each other, the influence of the voltage drop can be reduced even if a symmetrical configuration is not provided.

In the embodiment described above, the 1-st through k-th first device-side terminals 531 and the 1-st through k-th second device-side terminals 532 are wired in the first connector section 62, and the (k+1)-th through n-th first device-side terminals 531 and the (k+1)-th through n-th second device-side terminals 532 are wired in the second connector section 63. In contrast, it is also possible to wire the first device-side terminals 531 and the second device-side terminals 532 to respective connector sections different from each other. For example, the first connector section is disposed on the −Y side of the flexible board, the second connector section is disposed on the +Y side, the first device-side terminals 531 are wired to the first connector section located on the −Y side, and the second device-side terminals 532 are wired to the second connector section located on the +Y side. In such a configuration, it is also possible to input drive signals different in voltage from each other respectively to the first device-side terminals 531 and the second device-side terminals 532, and thus, it is also possible to deflect the acoustic pressure of the ultrasonic wave output from the ultrasonic device 5 to one side.

Although in the embodiment described above, there is illustrated the configuration in which the flexible board 6 includes the first connector section 62 and the second connector section 63, it is also possible to adopt a configuration provided with three or more connector sections, and so on.

For example, it is also possible to adopt a configuration in which a third connector section is disposed on the −Y side of the device connection section 61, and a fourth connector section is disposed on the +Y side of the device connection section 61 in addition to the first connector section 62 disposed on the −X side of the device connection section 61, and the second connector section 63 disposed on the +X side.

In the embodiment described above, there is illustrated the configuration in which the connectors 621 provided to the first connector section 62 and the connectors 631 provided to the second connector section 63 each have a long side parallel to the X direction, and the external connection terminals 622, 632 are arranged in the X direction, but this configuration is not a limitation. It is also possible for the connectors 621, 631 and the external connection terminals 622, 632 to be arranged along, for example, the Y direction.

In the embodiment described above, there is shown the example in which the ultrasonic device 5 is provided with the wiring board 53, and the wiring board 53 is provided with the device-side terminals to be connected to the respective terminals 513D, 514A provided to the ultrasonic substrate 51. In contrast, it is also possible to adopt a configuration in which the wiring board 53 is not provided, and the first connection part 614 and the second connection part 617 of the flexible board 6 are directly connected to the terminals 513D, 514A of the ultrasonic substrate 51.

In the embodiment described above, there is shown the example in which the ultrasonic device 5 transmits the ultrasonic wave from the substrate opening part 511A, and receives the ultrasonic wave entering the substrate opening part 511A. In contrast, it is also possible to adopt a configuration in which the sealing plate 52 is disposed on the substrate opening part 511A side, and the ultrasonic wave is output to the opposite side to the substrate opening part 511A.

Further, the transmission/reception column Ch provided with a plurality of ultrasonic transducers Tr is illustrated as the vibrator element provided to the ultrasonic device 5, but this example is not a limitation. For example, it is also possible that each of the ultrasonic transducers Tr can also be configured as a vibrator element.

Further, there is shown an example of the ultrasonic transducer Tr in which the ultrasonic wave is transmitted by vibrating the support film 512 with the piezoelectric element 513, and the ultrasonic wave is received by converting the vibration of the support film 512 into an electric signal with the piezoelectric element 513, but this example is not a limitation. For example, it is also possible to adopt a configuration in which the ultrasonic wave is transmitted and received by vibrating a bulk-type piezoelectric body, and further, it is also possible to adopt a configuration in which electrodes opposed to each other are provided to a pair of film members, and a cyclic drive voltage is applied between the electrodes to thereby vibrate the film members using electrostatic force.

In the embodiment described above, the ultrasonic measurement apparatus 1 taking an organ in a living body as the measurement object is illustrated as the ultrasonic apparatus, but this is not a limitation. For example, the configurations of the embodiment and the modified examples described above can be applied to a measurement apparatus taking a variety of types of structures as the measurement object, and performing detection of defects of the structures and inspections of aging of the structures. Further, the same applies to a measurement apparatus taking, for example, a semiconductor package or a wafer as the measurement object, and detecting the defects of the measurement object.

Besides the above, specific structures to be adopted when implementing the invention can be configured by arbitrarily combining the embodiment and the modified examples described above with each other, or can arbitrarily be replaced with other structures and so on within the range in which the advantages of the invention can be achieved.

The entire disclosure of Japanese Patent Application No. 2017-055391 filed Mar. 22, 2017 is expressly incorporated by reference herein.

What is claimed is:

1. An ultrasonic device unit comprising:
   an ultrasonic device including 1-st through n-th (n is an integer no smaller than 2) vibrator elements and 1-st through n-th device-side terminals connected correspondingly respectively to the vibrator elements, each of the vibrator elements including a plurality of ultrasonic elements arranged in a first direction, the vibrator elements being arranged in a second direction crossing the first direction; and
   a flexible printed wiring board being rectangular-shaped, the flexible printed wiring board being divided into a first connector section, a second connector section, and a device connection section, the device connection section being positioned between the first connector section and the second connector section, the flexible printed wiring board being folded at a first border between the first connector section and the device connection section, the flexible printed wiring board being folded at a second border between the second connector section and the device connection section, the ultrasonic device being mounted on the device connection section of the flexible printed wiring board, wherein the first connector section of the flexible printed wiring board has 1-st through k-th (k is an integer satisfying 1≤k<n) external connection terminals, the second connector section of the flexible printed wiring board has (k+1)-th through n-th external connection terminals, the 1-st through n-th device-side terminals of the ultrasonic device are connected to the device connection section, and wirings of the flexible printed wiring board connect the 1-st through n-th device-side terminals of the ultrasonic device to the corresponding 1-st through n-th external connection terminals, respectively, wherein the device-side terminals include a first group of the device-side terminals disposed on one end side in the first direction of the vibrator elements and a second group of the device-side terminals disposed on the other end side in the first direction of the vibrator elements, and an i-th device-side terminal of the first group of the device-side terminals and an i-th device-side terminal of the second group of the device-side terminals are connected to an i-th external connection terminal of the 1-st through n-th external connection terminals.

2. The ultrasonic device unit according to claim 1, wherein in the flexible printed wiring board, the first connector section, the device connection section, and the second connector section are arranged along the second direction.

3. The ultrasonic device unit according to claim 1, wherein the following is fulfilled:

$|(n-k)-k|/n \leq 0.2$.

4. The ultrasonic device unit according to claim 1, wherein the following is fulfilled:

$k=n/2$.

5. An ultrasonic probe comprising:

an ultrasonic device including 1-st through n-th (n is an integer no smaller than 2) vibrator elements and 1-st through n-th device-side terminals connected corresponding respectively to the vibrator elements, each of the vibrator elements including a plurality of ultrasonic elements arranged in a first direction, the vibrator elements being arranged in a second direction crossing the first direction;

a flexible printed wiring board being rectangular-shaped, the flexible printed wiring board being divided into a first connector section, a second connector section, and a device connection section, the device connection section being positioned between the first connector section and the second connector section, the flexible printed wiring board being folded at a first border between the first connector section and the device connection section, the flexible printed wiring board being folded at a second border between the second connector section and the device connection section, the ultrasonic device being mounted on the device connection section of the flexible printed wiring board; and a housing that houses the ultrasonic device and the flexible printed wiring board, wherein the first connector section of the flexible printed wiring board has 1-st through k-th (k is an integer satisfying 1≤k<n) external connection terminals, the second connector section of the flexible printed wiring board has (k+1)-th through n-th external connection terminals, the 1-st through n-th device-side terminals of the ultrasonic device are connected to the device connection section, and wirings of the flexible printed wiring board connect the 1-st through n-th device-side terminals of the ultrasonic device to the corresponding 1-st through n-th external connection terminals, respectively, wherein the device-side terminals include a first group of the device-side terminals disposed on one end side in the first direction of the vibrator elements and a second group of the device-side terminals disposed on the other end side in the first direction of the vibrator elements, and an i-th device-side terminal of the first group of the device-side terminals and an i-th device-side terminal of the second group of the device-side terminals are connected to an i-th external connection terminal of the 1-st through n-th external connection terminals.

6. The ultrasonic probe according to claim 5, wherein in the flexible printed wiring board, the first connector section, the device connection section, and the second connector section are arranged along the second direction.

7. The ultrasonic probe according to claim 5, wherein the following is fulfilled:

$|(n-k)-k|/n \leq 0.2$.

8. The ultrasonic probe according to claim 5, wherein the following is fulfilled:

$k=n/2$.

9. An ultrasonic apparatus comprising:

an ultrasonic device including 1-st through n-th (n is an integer no smaller than 2) vibrator elements and 1-st through n-th device-side terminals connected corresponding respectively to the vibrator elements, each of the vibrator elements including a plurality of ultrasonic elements arranged in a first direction, the vibrator elements being arranged in a second direction crossing the first direction;

a flexible printed wiring board being rectangular-shaped, the flexible printed wiring board being divided into a first connector section, a second connector section, and a device connection section, the device connection section being positioned between the first connector section and the second connector section, the flexible printed wiring board being folded at a first border between the first connector section and the device connection section, the flexible printed wiring board being folded at a second border between the second connector section and the device connection section, the ultrasonic device being mounted on the device connection section of the flexible printed wiring board;

a memory configured to store a program; and a processor configured to execute the program so as to control the ultrasonic device, wherein the first connector section of the flexible printed wiring board has 1-st through k-th (k is an integer satisfying 1≤k<n) external connection terminals, the second connector section of the flexible printed wiring board has (k+1)-th through n-th external connection terminals, the 1-st through n-th device-side terminals of the ultrasonic device are connected to the device connection section, and wirings of the flexible printed wiring board connect the 1-st through n-th device-side terminals of the ultrasonic device to the corresponding 1-st through n-th external connection terminals, respectively, wherein the device-side terminals include a first group of the device-side terminals disposed on one end side in the first direction of the vibrator elements and a second group of the device-side terminals disposed on the other end side in the first direction of the vibrator elements, and an i-th device-side terminal of the first group of the device-side terminals and an i-th device-side terminal of the second group of the device-side terminals are connected to an i-th external connection terminal of the 1-st through n-th external connection terminals.

10. The ultrasonic apparatus according to claim 9, wherein in the flexible printed wiring board, the first connector section, the device connection section, and the second connector section are arranged along the second direction.

11. The ultrasonic apparatus according to claim 9, wherein the following is fulfilled:
$|(n-k)-k|/n \leq 0.2$.

12. The ultrasonic apparatus according to claim 9, wherein the following is fulfilled:
$k=n/2$.

* * * * *